United States Patent [19]
Tachibana et al.

[11] Patent Number: 5,412,004
[45] Date of Patent: May 2, 1995

[54] SILICONE POLYMER, PASTE-LIKE SILICONE COMPOSITION, AND W/O-TYPE COSMETIC COMPOSITION COMPRISING THE SAME

[75] Inventors: Kiyomi Tachibana, Tokyo; Koji Sakuta; Kenichi Isobe, both of Annaka, all of Japan

[73] Assignees: Kose Corporation; Shin-Etsu Chemical Co., Ltd., both of Tokyo, Japan

[21] Appl. No.: 202,086

[22] Filed: Feb. 25, 1994

Related U.S. Application Data

[62] Division of Ser. No. 934,317, Aug. 25, 1992, abandoned.

[30] Foreign Application Priority Data

Nov. 21, 1991 [JP] Japan .................. 3-332641
Jul. 16, 1992 [JP] Japan .................. 3-189610
Jul. 16, 1992 [JP] Japan .................. 3-189611

[51] Int. Cl.$^6$ ................................. C08L 5/00
[52] U.S. Cl. ........................... 524/27; 524/56; 524/58; 524/267; 524/379; 524/385; 524/389; 514/844; 514/845; 514/846
[58] Field of Search ............. 524/267, 379, 385, 389, 524/56, 58, 27; 514/844, 845, 846

[56] References Cited

U.S. PATENT DOCUMENTS

| | | |
|---|---|---|
| 4,520,160 | 5/1985 | Brown . |
| 4,877,854 | 10/1989 | Hattori et al. . |
| 4,987,169 | 1/1991 | Kuwata et al. . |
| 4,990,560 | 2/1991 | Ikeno et al. . |
| 5,112,512 | 5/1992 | Nakamura . |
| 5,236,986 | 8/1993 | Sakuta . |

FOREIGN PATENT DOCUMENTS

| | | |
|---|---|---|
| 0298402 | 1/1989 | European Pat. Off. . |
| 0420253A2 | 4/1991 | European Pat. Off. . |
| 0501791A2 | 9/1992 | European Pat. Off. . |
| 4010281A1 | 10/1990 | Germany . |

Primary Examiner—Melvyn I. Marquis
Attorney, Agent, or Firm—Bacon & Thomas

[57] ABSTRACT

A silicone polymer, a paste-like silicone composition prepared by kneading the silicone polymer and a silicone oil under a shearing force, and a water-in-oil type cosmetic composition comprising the paste-like silicone composition as an oil phase component are disclosed. The silicone polymer is prepared by the addition polymerization of components comprising an organohydrogenpolysiloxane $R^1_a R^2_b H_c SiO_{(4-a-b-c)/2}$ (1) or $R^1_f H_g SiO_{(4-f-g)/2}$ (2) and a polyoxyalkylene $C_m H_{2m-1} O(C_2H_4O)_h(C_3H_6O)_i C_m H_{2m-1}$ (A) or an organopolysiloxane $R^1_j R^4_k SiO_{(4-j-k)/2}$ (B) the components, including (1) or (A) as an essential component. The silicone polymer can swell in silicone oils and function as a viscosity increasing agent for silicone oils.

20 Claims, No Drawings

SILICONE POLYMER, PASTE-LIKE SILICONE COMPOSITION, AND W/O-TYPE COSMETIC COMPOSITION COMPRISING THE SAME

This application is a Division of application Ser. No. 07/934,317, filed Aug. 25, 1992, now abandoned.

BACKGROUND OF THE INVENTION

1. Field of the Invention

The present invention relates to a silicone polymer, and, more particularly, to a silicone polymer swelling in silicone oil, a paste-like silicone composition comprised of said silicone polymer which is a stable and homogeneous water-in-oil type, and a cosmetic composition comprising said paste-like silicone composition.

2. Description of the Background Art

Silicone oils are used as a base oil for a number of compositions in a wide variety of fields, including medical products, cosmetics, and the like, because of their safety. In recent years, low viscosity silicone oils, particularly those having viscosities of 100 cS or lower, are attracting the attention due to their superior spreadability, excellent freshness, and high safety. Their applications to various compositions are under study.

A large amount of a viscosity-increasing agent must be added for the preparation of a paste-like or greasy silicone composition using such a low viscosity silicone oil as a base oil. The addition of a large amount of a viscosity-increasing agent, however, makes it difficult to obtain a smooth and homogeneous composition and produces a composition with a poor stability due to separation or issue of the low viscosity silicone oil from the composition.

In order to avoid this problem, many types of viscosity increasing agents to be used for low viscosity silicone oils have been proposed, including organic materials, e.g., fatty acid esters of dextrin (Japanese Patent Laid-open (ko-kai) Nos. 121764/1987, 143970/1987, 143971/1987, and 159489/1988), fatty acid esters of sucrose (Japanese Patent Laid-open (ko-kai) No. 235366/1988), trimethyl-silylated polyvinyl alcohols or trimethyl-silylated polysaccharides (Japanese Patent Laid-open (ko-kai) No. 240335/1987), cellulose ethers containing fatty acid ester groups (Japanese Patent Laid-open (ko-kai) No. 260955/1988); and inorganic materials, e.g., montmorillonite clays (Japanese Patent Laid-open (ko-kai) Nos. 45656/1987, 54759/1987, and 72779/1988). The use of these organic or inorganic materials as viscosity increasing agents, however, entails a problem of reducing the inherent characteristics of low viscosity silicone oils, such as excellent freshness and high spreadability.

Therefore, a method of producing a homogeneous paste-like composition by treating a specific type of silicone polymer as a viscosity increasing agent and a low viscosity silicone oil under a sharing force was recently proposed (Japanese Patent Laid-open (ko-kai) No. 43263/1990). This method, however, involves a problem in that the composition produced cannot homogeneously disperse water therein when water is added to it, even though it provides an excellent viscosity increasing effect. The use of a surfactant can be considered to ensure homogeneous dispersion of water which is an essential component in many medical or cosmetic compositions. In this case, however, it is difficult to effect stable and homogeneous dispersion of water into silicone oils. In addition, the use of surfactants is undesirable because many surfactants are irritative to the skin.

A first object of the present invention is therefore to provide a novel silicone polymer which is capable of converting a low viscosity silicone oil into a paste-like or greasy composition.

A second object of the present invention is to provide a novel paste-like silicone composition which is capable of dispersing water stably and homogeneously without using a surfactant.

A third object of the present invention is to provide a water-in-oil type cosmetic composition which imparting a fresh sensation upon use without stickiness and stable for a long period of time, and a water-in-oil type cosmetic composition having a superior water repellency and a capability of excellently retaining the make-up without running; both prepared by incorporating a low viscosity silicone oil in the oil phase in a stable manner.

The present inventors have conducted extensive studies in order to develop a silicone polymer which can produce a homogeneous paste-like composition swelling in silicone oil and capable of dispersing water. As a result, the present inventors have found that a polymer swelling in a silicone oil can be obtained by the addition polymerization of a mixture of an organohydrogenpolysiloxane having a polyoxyalkylene group in its molecule and an organ-opolysiloxane containing an aliphatic unsaturated group in its molecule, or a mixture of an organohydrogenpolysiloxane and a polyoxyalkylene containing an aliphatic unsaturated group ($C_mH_{2m-1}$ group) in its molecule, and that this polymer can act as a viscosity increasing agent for silicone oils and, if kneaded under a shearing force together with a silicone oil, can produce a paste-like silicone composition in which water is homogeneously and stably dispersed.

The present inventors have further found that if said mixture is subjected to the addition polymerization in the presence of a silicone oil having a viscosity of 100 cS or lower at 25° C. and/or a polyhydric alcohol, the resulting polymer exhibits even higher swellability in the silicone oil and that, if kneaded under a shearing force together with a silicone oil, this polymer permits water to more stably and homogeneously disperse into a paste-like silicone composition.

The present inventors further undertaken researches concerning the application of the above paste-like silicone composition to cosmetics.

SUMMARY OF THE INVENTION

Accordingly, an object of this invention is to provide a silicone polymer prepared by the addition polymerization of the following components (I) and (II):

(I) an organohydrogenpolysiloxane represented by the following formula (1),

wherein $R^1$ represents a substituted or unsubstituted alkyl, aryl, or aralkyl group having carbon atoms of 1–18, or a halogenated hydrocarbon group; $R^2$ represents a group,

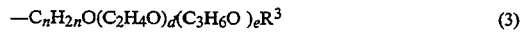

wherein $R^3$ is a hydrogen, a saturated aliphatic hydrocarbon group having 1–10 carbon atoms, or a group —(CO)—$R^5$ (wherein $R^5$ is a saturated aliphatic hydrocarbon group having 1-5 carbon atoms), d is an integer of 2-200, and e is an integer of 0-200, provided that d+e is 3-200, and n is 2-6; a is a value satisfying inequality $1.0 \leq a \leq 2.5$; b is a value satisfying inequality $0.001 \leq b \leq 1.0$; and c is a value satisfying inequality $0.001 \leq c \leq 1.0$; or an organohydrogenpolysiloxane represented by the following formula (2), $$R^1{}_f H_g SiO_{(4-f-g)/2} \tag{2}$$

wherein $R^1$ is the same as defined in formula (1), f is a value satisfying inequality $1.0 \leq f \leq 3.0$, and g is a value satisfying inequality $0.001 \leq g \leq 1.5$; or a mixture of said organohydrogenpolysiloxanes of formulas (1) and (2), and (II) a polyoxyalkylene represented by the following formula (A), $$C_m H_{2m-1} O(C_2H_4O)_h(C_3H_6O)_i C_m H_{2m-1} \tag{A}$$

wherein h is an integer of 2-200, i is an integer of 0-200, provided that h+i is 3-200, and m is 2-6, or an organopolysiloxane represented by the following formula (B), $$R^1{}_j R^4{}_k SiO_{(4-j-k)/2} \tag{B}$$

wherein $R^1$ is the same as defined in formula (1), $R^4$ is a monovalent hydrocarbon group having an aliphatic unsaturated bond at the terminal thereof and containing 2-10 carbon atoms, j is a value satisfying inequality $1.023 \; j \leq 3.0$, and k is a value satisfying inequality $0.001 \leq k \leq 1.5$, or a mixture of the polyoxyalkylene of formula (A) and the organopolysiloxane of formula (B), wherein at least one organohydrogenpolysiloxane of formula (1) or at least one polyoxyalkylene of formula (A) is contained as an essential component of the addition polymerization (herein referred to as the first invention).

Another object of the present invention is to provide a silicone polymer which is prepared by addition-polymerizing 100 parts by weight of the components defined in said first invention in the presence of 3-200 parts by weight of a low viscosity silicone oil having a viscosity of 100 cS or lower at 25° C. or a polyhydric alcohol, or both (herein referred to as the second invention).

Still another object of the present invention is to provide a paste-like silicone composition which can disperse water and is prepared by kneading 100 parts by weight of said silicone polymer and 10-1,000 parts by weight of a silicone oil under a shearing force (herein referred to as the third invention).

A further object of the present invention is to provide a water-in-oil type cosmetic composition comprising said paste-like silicone composition as an oil phase component and at least one water phase component (herein referred to as the fourth invention).

In a preferred embodiment of the fourth invention, said water-in-oil type cosmetic composition comprises (i) said paste-like silicone composition and (ii) silicic acid anhydride or hydrophobic silica, or both, as oil phase components, and at least one water phase component (herein referred to as the fifth invention).

In another preferred embodiment of the fourth invention, said water-in-oil type cosmetic composition comprises said paste-like silicone composition as an oil phase component and one or more components selected from the group consisting of saccharides, sugar alcohols, and inorganic salts, as water phase components (herein referred to as the sixth invention).

A further object of the present invention is to provide a water-in-oil type emulsion cosmetic composition comprising said paste-like silicone composition as an oil phase component, at least one water phase component, and a polyoxyalkylene-modified organopolysiloxane type surfactant (herein referred to as the seventh invention).

A still further object of the present invention is to provide a water-in-oil type cosmetic composition comprising said paste-like silicone composition as an oil phase component, at least one water phase component, and a cosmetic powder (herein referred to as the eighth invention).

Other objects, features and advantages of the invention will hereinafter become more readily apparent from the following description.

DETAILED DESCRIPTION OF THE INVENTION AND PREFERRED EMBODIMENTS

The silicone polymer of the first invention is prepared by the addition polymerization of either an organohydrogenpolysiloxane (1) or (2) or both and either a compound (A) or (B) or both having an aliphatic unsaturated group. It is essential that either the organohydrogenpolysiloxane or the compound having an aliphatic unsaturated group contain a polyoxyalkylene group. Therefore, the following combinations of either the organohydrogenpolysiloxane (1) or (2) or both and either the compound (A) or (B) or both having an aliphatic unsaturated group are possible.

(a) The combination of organohydrogenpolysiloxane of formula (1) and organopolysiloxane of formula (B).
(b) The combination of organohydrogenpolysiloxane of formula (2) and polyoxyalkylene of formula (A).
(c) The combination of organohydrogenpolysiloxane of formula (1) and polyoxyalkylene of formula (A).

The combination (a) is first illustrated in detail.

In formula (1), $R^1{}_a R^2{}_b H_c SiO_{(4-a-b-c)/2}$, which represents organohydrogenpolysiloxane containing a polyoxyalkylene group, $R^1$ is a substituted or unsubstituted alkyl, aryl, or aralkyl group having carbon atoms of 1-18, or a halogenated hydrocarbon group. Specifically, $R^1$ is selected from alkyl groups, e.g., methyl, ethyl, propyl, butyl, etc.; aryl groups, e.g., phenyl, tolyl, etc.; aralkyl groups, e.g., benzyl, phenetyl, etc.; and hydrogenated hydrocarbon groups with one or more hydrogen atoms of these alkyl, aryl, or aralkyl groups substituted by halogen atoms, e.g., chloromethyl, trifluoropropyl, etc. When a mixture of organohydrogenpolysiloxanes is used, different organohydrogenpolysiloxane may contain different $R^1$s. $R^2$ represents a polyoxyalkylene group of the following formula (3), $$-C_n H_{2n} O(C_2H_4O)_d(C_3H_6O)_e R^3 \tag{3}$$

wherein $R^3$ is a hydrogen, a saturated aliphatic hydrocarbon group having 1-10 carbon atoms, e.g., methyl, ethyl, propyl, butyl, pentyl, hexyl, heptyl, octyl, etc., or a group $—(CO)—R^5$ (wherein $R^5$ is a saturated aliphatic hydrocarbon group having 1-5 carbon atoms), d is an integer of 2-200, e is an integer of 0-200, provided that d+e is 3-200, and n is 2-6. The ratio d/e is desirably 1 or more in order to ensure good dispersion of water in the paste-like silicone composition prepared by kneading the obtained polymer and a silicone oil under a shearing force.

If the value a in formula (1) is less than 1.0, the obtained polymer cannot sufficiently swell in silicone oils; if greater than 2.5, the paste-like silicone composition prepared by kneading the obtained polymer and a silicone oil under a shearing force cannot well disperse water therein. Therefore, a should be a value satisfying inequality $1.0 \leq a \leq 2.5$, and preferably a value of 1.0-2.0. If the value b is less than 0.001, the paste-like silicone composition prepared by kneading the obtained polymer and a silicone oil under a shearing force cannot well disperse water therein; if greater than 1.0, the obtained polymer cannot sufficiently swell in silicone oils. Thus, b should be a value satisfying inequality $0.001 \leq b \leq 1.0$, and preferably a value of 0.005-1.0. The value of c less than 0.001 makes the formation of the three dimensional structure in the polymer obtained by the addition polymerization difficult, impairing the viscosity increasing capability of the polymer. If the value c is greater than 1.0, on the other hand, the cross-linking density of the three dimensional structure formed by the addition polymerization becomes too high for the polymer to retain silicone oils in a stable manner. Therefore, c should be a value satisfying inequality $0.001 \leq c \leq 1.0$, and preferably a value of 0.005-1.0.

The other component which is combined with the organohydrogenpolysiloxane of formula (1) is organopolysiloxane of the following formula (B), $$R^1_j R^4_k SiO_{(4-j-k)/2} \tag{B}$$

wherein $R^1$ is the same as defined in formula (1), $R^4$ is a monovalent hydrocarbon group having an aliphatic unsaturated group, e.g., vinyl group, allyl group, etc., at the terminal thereof and containing 2-10 carbon atoms. If j in formula (B) is less than 1.0, the cross-linking density of the three dimensional structure formed by the addition polymerization becomes too high for the polymer to retain silicone oils in a stable manner; if it is greater than 3, the formation of the three dimensional structure in the polymer obtained by the addition polymerization is insufficient, resulting in the polymer with a poor viscosity increasing capability. Therefore, j should be a value satisfying inequality $1.0 \leq j \leq 3.0$, and preferably a value of 1.0-2.5. Regarding the value k, if this value is less than 0.001, the formation of the three dimensional structure in the target polymer obtained by the addition polymerization becomes difficult, resulting in the polymer with a poor viscosity increasing capability; if greater than 1.5, on the other hand, the cross-linking density of the three dimensional structure in the target polymer formed by the addition polymerization becomes too high for the polymer to retain silicone oils in a stable manner. Therefore, k should be a value satisfying inequality $0.001 \leq k \leq 1.5$, and preferably a value of 0.005-1.0.

The mixture of organohydrogenpolysiloxane of formula (1) and organopolysiloxane of formula (B) is hereinafter referred to as Mixture-I.

Illustrating the above combination (b), the combination of organohydrogenpolysiloxane of formula (2) and polyoxyalkylene of formula (A), in organohydrogenpolysiloxane of formula (2), $$R^1_f H_g SiO_{(4-f-g)/2} \tag{2}$$

$R^1$ is the same as defined in formula (1), f is a value satisfying inequality $1.0 \leq f \leq 3.0$, and g is a value satisfying inequality $0.001 \leq g \leq 1.5$. If f is less than 1.0, the obtained polymer cannot sufficiently swell in silicone oils; if greater than 3.0, on the other hand, the formation of the three dimensional structure in the polymer obtained by the addition polymerization becomes difficult, and a only a polymer with a poor viscosity increasing capability is produced. Therefore, f should be a value satisfying inequality $1.0 \leq f \leq 3.0$, and preferably a value of 1.0-2.5. The value of g less than 0.001 makes the formation of the three dimensional structure in the polymer obtained by the addition polymerization difficult, impairing the viscosity increasing capability of the polymer. The value of g greater than 1.5, on the other hand, makes the cross-linking density of the three dimensional structure formed by the addition polymerization too high for the polymer to retain silicone oils in a stable manner. Therefore, g should be a value satisfying inequality $0.001 \leq c \leq 1.5$, and preferably a value of 0.005-1.0.

In polyoxyalkylenes of the following formula (A), $$C_m H_{2m-1} O(C_2 H_4 O)_h (C_3 H_6 O)_i C_m H_{2m-1} \tag{A}$$

h is an integer of 2-200, and preferably 5-100; and i is an integer of 0-200, and preferably 0-100. The ratio h/i is preferably 1 or more and m is 2-6, and preferably 3-6, in order to ensure good dispersion of water in the resulting polymer.

The mixture of orgahohydrogenpolysiloxane of formula (2) and polyoxyalkylene of formula (A) is hereinafter referred to as Mixture-II.

For combination (c), the combination of the above-mentioned organohydrogenpolysiloxane of formula (1) and polyoxyalkylene of formula (A) can be given as an example. The mixture of organohydrogenpolysiloxane of formula (1) and polyoxyalkylene of formula (A) is hereinafter referred to as Mixture-III.

The silicone polymer of the second invention can be obtained by the addition polymerization of Mixture-I, Mixture-II, or Mixture-III in the presence of a low viscosity silicone oil having a viscosity of 100 cS or smaller at 25° C. or a polyhydric alcohol, or both. Given as examples of silicone oils having a viscosity of 100 cS or smaller at 25° C. are linear or branched methylpolysiloxane, methylphenylpolysiloxane, ethylpolysiloxane, ethylmethylpolysiloxane, ethylphenylpolysiloxane, cyclic dimethylpolysiloxane, e.g., octamethylcyclotetrasiloxane, decamethylcyclopentasiloxane, etc.; and the like. The viscosity of these silicone oils is not specifically limited so long as it is 100 cS or lower, preferably 50 cS or lower, at 25° C. These silicone oils can be used either singly or in mixture.

Polyhydric alcohols which can be used for the above addition polymerization include ethylene glycol, 1,3-butylene glycol, propylene glycol, dipropylene glycol, glycerin, diglycerin, and the like. They can be used singly or two or more of them can be used in combination.

In the second invention, in which the addition polymerization of Mixture-I; Mixture-II, or Mixture-III is carried out in the presence of a low viscosity silicone oil having a viscosity of 100 cS or lower at 25° C. or a polyhydric alcohol, or both, the amount of the low viscosity silicone oil and polyhydric alcohol used is 3-200 parts by weight for 100 parts by weight of Mixture-I, -II, or -III. If this amount is less than 3 parts by weight, sufficient effects intended by the present invention cannot be obtained; if greater than 200 parts by weight, the addition polymerization reaction is inhibited, resulting in a poor conversion and producing a polymer product with an insufficient viscosity increasing effect.

In the above addition polymerization, the presence of a low viscosity silicone oil or a polyhydric alcohol results in a silicone polymer containing such a low viscosity silicone oil or a polyhydric alcohol.

In the addition polymerization in the first and second inventions, said Mixture-I, -II, or -III is reacted in the presence of a known platinum catalyst, e.g., chloroplatinic acid, alcohol-modified chloroplatinic acid, or a chloroplatinic acid-vinylsiloxane complex, or in the presence of a rhodium catalyst, at room temperature or with heating at 50°–150° C.

An organic solvent may optionally be used in the reaction. Organic solvents which can be used include aliphatic alcohols, e.g., methanol, ethanol, 2-propanol, butanol, etc., aromatic hydrocarbons, e.g., benzene, toluene, xylene, etc.; aliphatic or alicyclic hydrocarbons, e.g., n-pentane, n-hexane, cyclohexane, etc., halogenated hydrocarbons, e.g., dichloromethane, chloroform, carbon tetrachloride, trichloroethane, trichloroethylene, fluorochloro hydrocarbons, etc., and the like. Of these, ethanol is preferable taking into consideration the fact that the resulting silicone polymers are applied to medical products and cosmetics.

The paste-like, homogeneous silicone composition, which is the subject of the third invention, can be prepared by mixing 100 parts by weight of the silicone polymer of the first or the second invention and 10–1,000 parts by weight, preferably 20–500 parts by weight, of a silicone oil and kneading the mixture under a shearing force. This paste-like silicone composition can disperse powders and pigments having specific gravities different from that of silicone oils, and can hold them therein in a stable manner without precipitating them. Owing to this characteristic, the composition is useful as a base material for creams, cakes, and the like used in cosmetics and quasi medical products.

Silicone oils used for the preparation of the paste-like silicone composition may be either linear or branched, and include methylpolysiloxane, methylphenylpolysiloxane, ethylpolysiloxane, ethylmethylpolysiloxane, ethylphenylpolysiloxane, cyclic dimethylpolysiloxane, e.g., octamethylcyclotetrasiloxane, decamethylcyclopentasiloxane, etc.; and the like. They may be used either singly or as a mixture of two or more of them. A homogeneous, paste-like composition cannot be obtained, if the amount of the silicone oil is smaller than 10 parts by weight. The amount exceeding 1,000 parts by weight does not yield sufficient viscosity increasing capability. Thus, the amount of silicone oils should be in the range of 10–1,000 parts by weight for 100 parts by weight of the silicone polymer.

The paste-like silicone composition of the third invention thus obtained has a smooth and homogeneous outward appearance. If the shearing force is not applied or applied only insufficiently, the two components are not mingled together due to insufficient swelling of the polymer in the silicone oil, resulting in a nonhomogeneous product with no smoothness both in the outward appearance and in the sensation to the touch.

A triple roll mill, double roll mill, sand grinder, colloid mill, Gaurin homogenizer, or the like can be used for the kneading under the shearing force. The use of a triple roll mill is especially preferable.

The water-in-oil type cosmetic composition of the fourth invention is characterized by incorporating said paste-like silicone composition in oil phase components. Although there are no limitations to the amount of the paste-like silicone composition to be incorporated, a preferable range is 10–9% by weight (hereinafter simply referred to as %) of the oil phase components.

Beside the paste-like silicone composition, oily materials conventionally used for cosmetic compositions can be incorporated as the oil phase components to the extent that they do not interfere the homogeneity of the oil phase. Such oily materials may be liquid oils, semi-solid oils, or solids oils, and can be used either singly or in combination of two or more of them. Given as examples of liquid and semi-solid oils are liquid paraffin, squalane, castor oil, isopropyl myristate, isopropyl palmitate, lanolin, petrolatum, olive oil, jojoba oil, macadamia nut oil, mink oil, turtle oil, almond oil, safflower oil, avocado oil, octyldodecyl myristate, cetyl 2-ethylhexanoate, fatty acid esters of glycerine (e.g., 2-ethylhexanoic triglyceride, isostearic diglyceride), fatty acid esters of propylene glycol (e.g., dicapriric propylene glycol), fatty acid esters of dipentaerythritol, oleic acid, oleyl alcohol, and the like.

As solid oils, hydrocarbons, waxes, hydrogenated oils, higher fatty acids, higher alcohols, and the like can be used. Specific examples include solid paraffin wax, ceresine wax, microcrystalline wax, carnauba wax, candelilla wax, bees wax, wood wax, whale wax, polyethylene wax, hydrogenated castor oil, rhodinic acid ester of pentaerythritol, stearic acid, lauric acid, myristic acid, behenic acid, cetyl alcohol, stearyl alcohol, lauryl alcohol, and the like.

Furthermore, an oil gelling agent may also be added to the oil phase in order to obtain a water-in-oil type cosmetic composition of solid or semi-solid type. Oil gelling agents which can be used include metal soaps, e.g., aluminum stearate, magnesium stearate, etc., fatty acid esters of polysaccharide, e.g., sucrose palmitate, starch palmitate, etc., montmorillonite clays, e.g., montmorillonite modified with dioctadecyldimethylammonium, montmorillonite modified with dihexadecyldimethylammonium, and the like.

The oil phase components are incorporated in the water-in-oil type cosmetic composition in an amount of 10–99%. If less than 10%, it is difficult to make the composition water-in-oil type; if more than 99%, the cosmetic composition is a very heavy to the touch.

The addition of silicic acid anhydride or hydrophobic silica to the oil phase components of the water-in-oil type cosmetic composition, according to the fifth invention, remarkably promotes the stability while keeping the excellent sensation upon use of the paste-like silicone composition.

Silicic acid anhydride and hydrophobic silica used here may be those conventionally used in cosmetic compositions. Commercial products such as Aerosil 200, Aerosil 300 (trademarks, manufactured by Degussa Co.), or the like can be used as a suitable silicic acid anhydride. As hydrophobic silica, commercially available silicone-treated silica such as CAB-0-SIL TS-530 (trimethylsiloxylated silica: trademark, manufactured by Cabbot Co.), Aerosil R-972 (dimethylsiloxylated silica: trademark, manufactured by Degussa Co.), Aerosil R-805 (octylsiloxylated silica: trademark, manufactured by Degussa Co.), Aerosil R-202 (silicone oil treated silica: trademark, manufactured by Degussa Co.), and the like are commercially available and can be suitably used.

An effective amount of silicic acid anhydride or hydrophobic silica to be incorporated is in the range of 0.01–10% in the oil phase components. An amount exceeding 10% is undesirable, since the sensation of the product upon use is impaired and its stability is lowered.

The water-in-oil type cosmetic composition of the present invention may contain, as water phase components, water as a main component and various water soluble components in an amount of 1–90%. If less than 1%, such an incorporation of water is effectively nil; if more than 90%, it is difficult to make the composition water-in-oil type. The addition of one or more components selected from the group consisting of sugars, sugar alcohols, and inorganic salts as water phase components remarkably improves the stability of the composition over time without the addition of silicic acid anhydride and hydrophobic silica (hereinafter referred to as the sixth invention).

Given as saccharides used here are monosaccharide, disaccharide, oligosaccharide, polysaccharide, such as glucose, fructose, galactose, xylose, maltose, sucrose, lactose, starch, dextrin, and the like; as sugar alcohols, sorbitol, mannitol, maltitol, and the like; and as inorganic salts, sodium, potassium, calcium, magnesium, aluminum, or zinc salts of hydrochloric acid, sulfuric acid, carbonic acid, nitric acid, or the like.

The effective amount of saccharides, sugar alcohols, and inorganic salts to be added is 0.1–20% of the total amount of the oil phase components. An amount exceeding 20% makes the resulting cosmetic composition sticky and impairs the sensation upon use.

Even though the water-in-oil type cosmetic composition of the present invention can disperse water easily therein without the addition of a surfactant, a low irritant nonionic surfactant may be incorporated in order to retain the water-in-oil system more stably. Preferable surfactants are polyoxyalkylene-modified organopolysiloxane type surfactants (the seventh invention).

Polyoxyalkylene-modified organopolysiloxane type surfactants which can be used are those which are liquid or paste at normal temperature. Specific examples include compounds represented by the following formulas (4)–(6).

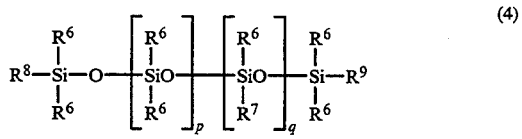

(4)

wherein $R^6$ represents an alkyl group having 1–5 carbon atoms or a phenyl group, $R^7$ is a group —$(CH_2)_r$—O—$(C_2H_4O)_s$—$(C_3H_6O)_t$—$R^{10}$ (wherein $R^{10}$ is a hydrogen or an alkyl group having 1–5 carbon atoms, r is a number of 1–5, s is a number of 1–50, and t is a number of 0–30), $R^8$ and $R^9$ are the same as either $R^6$ or $R^7$, p is a number of 5–300, and q is a number of 0–50, provided that when q is 0, at least one of $R^8$ and $R^9$ is the same as $R^7$ and provided further that not all $R^6$s can be phenyl group.

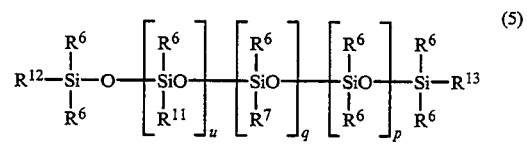

(5)

wherein $R^6$, $R^7$, p and q are the same as defined in formula (4), $R^{11}$ is an alkyl group having 2–20 carbon atoms, $R^{12}$ and $R^{13}$ are the same as at least one of $R^6$, $R^7$ and $R^{11}$ and u is a number of 1–30, provided that when q is 0, at least one of $R^{12}$ and $R^{13}$ is the same as $R^7$ and further that not all R6s can be phenyl group.

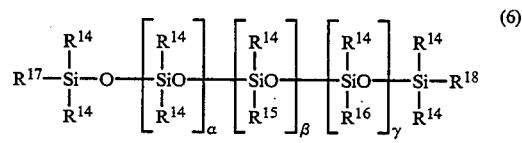

(6)

wherein $R^{14}$ represents an alkyl group having 1–4 carbon atoms $R^{15}$ is a group —$Q^1$—O—$(C_2H_4O)_x$—$(C_3H_6O)_y$—$R^{19}$(wherein $Q^1$ is a hydrocarbon group having 1–4 carbon atoms, $R^{19}$ is a hydrogen, an alkyl group having 1–4 carbon atoms, or an acetyl group, x is an integer of 1 or more, and y is an integer of 0 or more), $R^{16}$ is a group —$Q^2$—O—$R^{20}$ (wherein Q2 is a hydrocarbon group having 1–4 carbon atoms and $R^{20}$ is a hydrocarbon group having 8–30 carbon atoms), $R^{17}$ and $R^{18}$ are the same as at least one of $R^{14}$, $R^{15}$, and $R^{16}$ $\alpha$ is an integer of 0 or more, and $\beta$ and $\gamma$ are integers 1 or more.

Compounds represented by the above formula (4) are called polyether-modified silicone, exemplified by Silicon KF-945A (trademark, a product of Shin-etsu Chemical Co.), Silicon SH-3772C (trademark, a product of Toray-Dow Corning Silicone Co.), and the like.

Compounds represented by the above formula (5) are called alkylpolyether-modified silicone, exemplified by Abil WE-09 (trademark, a product of Goldschumit Co.) and the like.

Compounds represented by the above formula (6) are polyoxyalkylene alkyl ether-comodified organopolysiloxanes. They can be easily produced from methylhydrogenpolysiloxane by the co-modification with polyoxyalkylene allyl ether and allylalkyl ether, for example, according to the method of Reference Examples described hereinafter.

Since these types of polyoxyalkylene-modified organopolysiloxane type surfactants possess good mutual solubility with the paste-like silicone composition in the oil phase, they can provide excellent stability.

These surfactants are preferably added to the cosmetic composition of the present invention in an amount of 0.01–10%, and particularly preferably 0.5–5%.

According to the eighth invention of the present application, various kinds of cosmetic powders can be incorporated into the water-in-oil type cosmetic composition of the fourth invention.

There are no specific limitations as to the cosmetic powders to be used. Body pigments, inorganic white pigments, inorganic colored pigments, organic pigments, organic powders, pearling agents, or the like can be used. Specific examples are talc, kaolin, mica, magnesium carbonate, calcium carbonate, magnesium silicate, aluminum magnesium silicate, silica, titanium dioxide, zinc oxide, red iron oxide, yellow iron oxide, black iron oxide, ultramarine blue, tar pigment, nylon powder, polyethylene powder, polymethylmethacrylate powder, polystyrene powder, polytetrafluoroethylene powder, silk powder, crystalline cellulose, starch, titanated mica, iron oxide titanated mica, bismuth oxychloride, and the like.

These cosmetic powders may be used in an amount of 1–40%, and preferably 5–25%.

Preferred cosmetic compositions containing a cosmetic powder, which is the eighth invention, are those comprising the following components (a)–(e).

(a) a semisolid oil or a liquid oil, or both,
(b) a solid oil or an oil gelling agent, or both,
(c) the above-mentioned paste-like silicone composition,
(d) at least one water phase component, and
(e) a cosmetic powder.

The amount of the oil components (a) plus (b) is preferably 5–40%, and particularly preferably 15–30%, of the total amount of the cosmetic composition. Compositions containing an amount of oil components less than 5% does not function as an oily make-up cosmetic. If this amount is greater than 40%, the product is too oily, providing an impaired sensation upon use. Solid oils and oil gelling agents, the component (b), are preferably used in an amount of 5–50% in the total amount of the oil phase components and may be used either singly or in combination.

The amount of the paste-like silicone composition, the component (c), is preferably 5–60%, particularly preferably 15–40%. If this amount is smaller than 5%, the resulting cosmetic composition cannot stably hold large amounts of low viscosity silicone oils and water; if greater than 60%, the sensation upon use is impaired.

The amount of water, the component (d), is preferably 5–80%, and particularly preferably 10–60%, of the total amount of the cosmetic composition. If the amount of water is smaller than 5%, the waterish sensation upon use cannot be obtained; if greater than 80%, the stability over time is impaired.

Besides the above components, various components conventionally used for cosmetics can be optionally incorporated into the water-in-oil type cosmetic composition of the present invention to the extent that such incorporation does not impair the intended effects of the present invention. Such optional components include conventionally used aqueous components and oil components, e.g., moisturizers, preservatives, anti-oxidants, UV absorbers, skin-improvers, perfumes, water soluble polymer, tar colorants, and the like.

The water-in-oil type cosmetic compositions of the present invention can be prepared by preparing the paste-like silicone composition in advance, and by mixing it with other components according to a conventional method.

The silicone polymer of the present invention can well swell in silicone oils and function as a good viscosity increasing agent for silicone oils. The paste-like silicone composition can disperse powders and pigments having specific gravities different from that of silicone oils, and can hold them therein in a stable manner without precipitating them. Therefore, the water-in-oil type cosmetic compositions in which this paste-like silicone composition in oil phase components is incorporated can well spread and provide a moistened sensation without stickiness. In addition, they are extremely stable over time.

Other features of the invention will become apparent in the course of the following description of the exemplary embodiments which are given for illustration of the invention and are not intended to be limiting thereof.

EXAMPLES

Synthetic Example 68 g of organohydrogenpolysiloxanes of which the average composition is shown by the compound of the following formula (7),

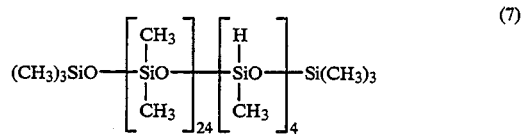

100 g of ethanol, 32 g of polyoxyalkylenes of which the average composition is shown by a compound of formula $CH_2=CHCH_2O\,(C_2H_4O)_{10}CH_3$, and 0.3 g of 3 wt % solution of chloroplatinic acid in ethanol were charged into a reaction vessel and stirred for 2 hours while keeping the internal temperature at 70°–80° C., followed by evaporation of the solvent under reduced pressure to obtain organohydrogenpolysiloxanes of which the average composition is shown by the compound of the following formula (8).

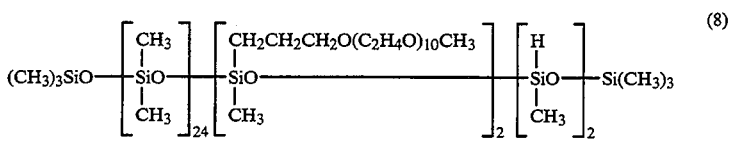

Example 1

100.0 g of organohydrogenpolysiloxanes of which the average composition is shown by the compound of the above formula (8), 100.0 g of ethanol, 28.9 g of dimethylpolysiloxanes of which the both ends were sealed by dimethylvinylsilyl groups and of which the average composition is shown by the compound of the following formula (9),

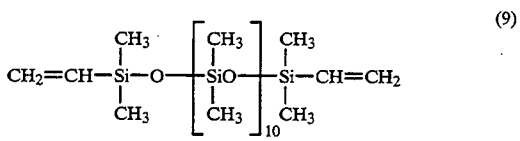

and 0.3 g of 3 wt % solution of chloroplatinic acid in ethanol were charged into a reaction vessel and stirred for 2 hours while keeping the internal temperature at 70°–80° C., followed by evaporation of the solvent under reduced pressure to obtain an elastic silicone polymer. 20 parts by weight of this silicone polymer and 80 parts by weight of dimethylpolysiloxane (viscosity at 25° C.: 6 cSt) were mixed and dispersed, and thoroughly kneaded by a triple roll mill under a shearing force to obtain a silicone composition. This composition was a homogeneous paste-like material, smooth to the touch and having a viscosity of 32,000 cP.

Fifty parts by weight of the paste-like silicone composition was mixed with 50 parts by weight of water. The water was easily dispersed by merely stirring the mixture to give a homogeneous creamy composition.

For comparison, the dispersed mixture with the same composition as above; 20 parts by weight of the silicone polymer and 80 parts by weight of dimethylpolysiloxane, was stirred for 2 hours at room temperature by a planetary mixer instead of a triple roll mixer. The polymer did not swell homogeneously, failing to produce a paste-like composition with a smooth sensation. Water added to the resulting mixture could hardly disperse, and oil and water were separated into two layers.

The above results demonstrate that only an application of a sufficient shearing force permits the silicone polymer of the present invention to swell and homogeneously disperse in a silicone oil, providing a paste-like silicone composition with an increased viscosity which gives a smooth sensation. Such a paste-like silicone composition cannot be produced under any conditions without a shearing force.

Example 2

100.0 g of organohydrogenpolysiloxanes of which the average composition is shown by the compound of the following formula (10),

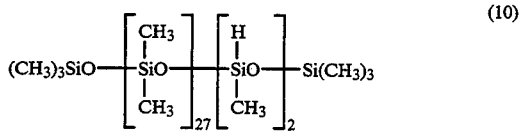

62.0 g of ethanol, 23.6 g of polyoxyalkylene of which the average composition is shown by the compound of the following formula (11),

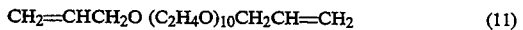

$$CH_2=CHCH_2O\ (C_2H_4O)_{10}CH_2CH=CH_2 \quad (11)$$

and 0.3 g of 3 wt % solution of chloroplatinic acid in ethanol were charged into a reaction vessel and processed in the same manner as in Example 1 to obtain silicone polymer particles.

33 parts by weight of this silicone polymer and 67 parts by weight of dimethylpolysiloxane (viscosity at 25° C.: 6 cSt) were mixed and dispersed, and thoroughly kneaded by a triple roll mill under a shearing force to obtain a silicone composition. This composition was a homogeneous paste-like material, smooth to the touch and having a viscosity of 24,800 cP. 50 parts by weight of this paste-like silicone composition was mixed with 50 parts by weight of water. The water was easily dispersed by merely stirring the mixture to give a homogeneous creamy composition.

Example 3

100 g of organohydrogenpolysiloxanes of which the average composition is shown by the compound of formula (7) used in Synthetic Example, 75 g of ethanol, 49.4 g of polyoxyalkylenes of which the average composition is shown by the compound of formula (11) used in Example 2, and 0.3 g of 3 wt % solution of chloroplatinic acid in ethanol were charged into a reaction vessel and processed in the same manner as in Example 1 to obtain silicone polymer particles.

33 parts by weight of this silicone polymer and 67 parts by weight of dimethylpolysiloxane (viscosity at 25° C.: 6 cSt) were mixed and dispersed, and thoroughly kneaded by a triple roll mill under a shearing to obtain a silicone composition. This composition was a homogeneous paste-like material, smooth to the touch and having a viscosity of 10,600 cP. 50 parts by weight of the paste-like silicone composition was mixed with 50 parts by weight of water. The water was easily dispersed by merely stirring the mixture to give a homogeneous creamy composition.

Example 4

100 g of organohydrogenpolysiloxanes of which the average composition is shown by the compound of the following formula (12),

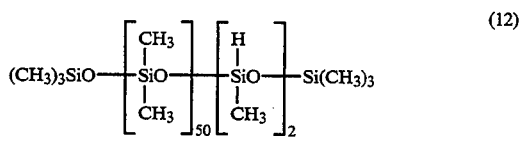

57 g of ethanol, 13.5 g of polyoxyalkylenes of which the average composition is shown by the compound of formula (11) used in Example 2, and 0.3 g of 3 wt % solution of chloroplatinic acid in ethanol were charged into a reaction vessel and processed in the same manner as in Example 1 to obtain silicone polymer particles.

20 parts by weight of this silicone polymer and 80 parts by weight of dimethylpolysiloxane (viscosity at 25° C.: 6 cSt) were mixed and dispersed, and thoroughly kneaded by a triple roll mill under a shearing force to swell the silicone polymer, thus obtaining a silicone composition. This composition was a homogeneous paste-like material, smooth to the touch and having a viscosity of 22,800 cP. 50 parts by weight of the paste-like silicone composition was mixed with 50 parts by weight of water. The water was easily dispersed by merely stirring the mixture to give a homogeneous creamy composition.

Example 5

100.0 g of organohydrogenpolysiloxanes prepared in Synthetic Example, 58 g of ethanol, 17.7 g of polyoxyalkylene of the following formula (13),

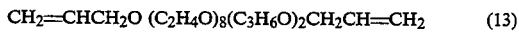

$$CH_2=CHCH_2O\ (C_2H_4O)_8(C_3H_6O)_2CH_2CH=CH_2 \quad (13)$$

and 0.3 g of 3 wt % solution of chloroplatinic acid in ethanol were charged into a reaction vessel and processed in the same manner as in Example 1 to obtain silicone polymer particles.

20 parts by weight of this silicone polymer and 80 parts by weight of dimethylpolysiloxane (viscosity at 25° C.: 10 cSt) were mixed and dispersed, and thoroughly kneaded by a triple roll mill under a shearing force to swell the polymer, thus obtaining a silicone composition. This composition was a homogeneous paste-like material, smooth to the touch and having a viscosity of 15,000 cP. 50 parts by weight of the paste-like silicone composition was mixed with 50 parts by Weight of water. The water was easily dispersed by merely stirring the mixture to give a homogeneous creamy composition.

Example 6

100 g of organohydrogenpolysiloxanes of which the average composition is shown by the compound of the following formula (14),

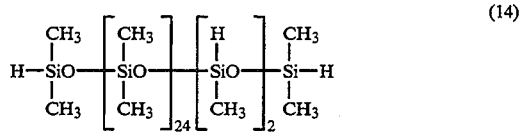
(14)

76 g of ethanol, 53 g of polyoxyalkylene of which the average composition is shown by formula (11) used in Example 2, and 0.3 g of 3 wt % solution of chloroplatinic acid in ethanol were charged into a reaction vessel and processed in the same manner as in Example 1 to obtain silicone polymer particles.

30 parts by weight of this silicone polymer and 70 parts by weight of decamethylcyclopentasiloxane (viscosity at 25° C.: 2 cSt) were mixed and dispersed, and thoroughly kneaded by a triple roll mill under a shearing force to swell the silicone polymer, thus obtaining a silicone composition. This composition was a homogeneous paste-like material, smooth to the touch and having a viscosity of 18,000 cP. 50 parts by weight of the paste-like silicone composition was mixed with 50 parts by weight of water. The water was easily dispersed by merely stirring the mixture to give a homogeneous creamy composition.

Example 7

100 g of organohydrogenpolysiloxanes of which the average composition is shown by formula (10) used in Example 2, 103.0 g of ethanol, 23.6 g of polyoxyalkylenes of which the average composition is shown by formula (11) used in Example 2, 82.4 g of dimethylpolysiloxane (viscosity at 25° C.: 6 cSt), and 0.3 g of 3 wt % solution of chloroplatinic acid in ethanol were charged into a reaction vessel and processed in the same manner as in Example 1 to obtain a silicone polymer.

100 parts by weight of this silicone polymer and 100 parts by weight of dimethylpolysiloxane (viscosity at 25° C.: 6 cSt) were mixed and dispersed, and thoroughly kneaded by a triple roll mill under a shearing force to swell the silicone polymer, thus obtaining a silicone composition. This composition was a homogeneous paste-like material, smooth to the touch and having a viscosity of 82,800 cP. 50 parts by weight of the paste-like silicone composition was mixed with 50 parts by weight of water. The water was easily dispersed by merely stirring the mixture to give a homogeneous creamy composition.

Example 8

100 g of organohydrogenpolysiloxanes of which the average composition is shown by formula (12) used in Example 4,. 95.0 g of ethanol, 13.5 g of polyoxyalkylenes of which the average composition is shown by formula (11) used in Example 2, 75.7 g of dimethylpolysiloxane (viscosity at 25° C.: 5 cSt), and 0.3 g of 3 wt % solution of chloroplatinic acid in ethanol were charged into a reaction vessel and processed in the same manner as in Example 1 to obtain a silicone polymer.

100 parts by weight of this silicone polymer and 200 parts by weight of octamethylcyclotetrasiloxane (viscosity at 25° C.: 6 cSt) were mixed and dispersed, and thoroughly kneaded by a triple roll mill under a shearing force to obtain a silicone composition. This composition was a homogeneous paste-like material, smooth to the touch and having a viscosity of 44,000 cP. 50 parts by weight of this paste-like silicone composition was mixed with 50 parts by weight of water. The water was easily dispersed by merely stirring the mixture to give a homogeneous creamy composition.

Example 9

100 g of organohydrogenpolysiloxanes of which the average composition is shown by the compound of the following formula (15),

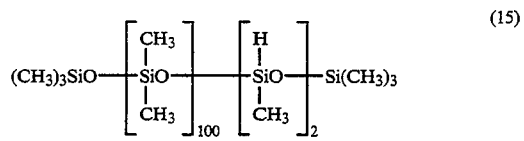
(15)

74.0 g of ethanol, 18.5 g of polyoxyalkylenes of which the average composition is shown by the following formula (16),

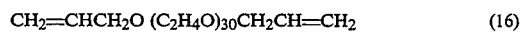

$$CH_2=CHCH_2O\ (C_2H_4O)_{30}CH_2CH=CH_2 \qquad (16)$$

29.6 g of dimethylpolysiloxane (viscosity at 25° C.: 6 cSt), and 0.3 g of 3 wt % solution of chloroplatinic acid in ethanol were charged into a reaction vessel and processed in the same manner as in Example 1 to obtain silicone polymer.

100 parts by weight of this silicone polymer and 200 parts by weight of phenyltris(trimethylsiloxy)silane were mixed and dispersed, and thoroughly kneaded by a triple roll mill under a shearing force to obtain a silicone composition. This composition was a homogeneous paste-like material, smooth to the touch and having a viscosity of 25,500 cP. 50 parts by weight of this paste-like silicone composition was mixed with 50 parts by weight of water. The water was easily dispersed by merely stirring the mixture to give a homogeneous creamy composition.

Example 10

100 g of organohydrogenpolysiloxanes of which the average composition is shown by formula (8) prepared in Synthetic Example, 72.0 g of ethanol, 28.9 g of dimethylpolysiloxane of which the both ends were sealed by dimethylvinylsilyl groups and of which the average composition is shown by the compound of formula (9), used in Example 1, 14.3 g of dimethylpolysiloxane (viscosity at 25° C.: 30 cSt), and 0.3 g of 3 wt % solution of chloroplatinic acid in ethanol were charged into a reaction vessel and processed in the same manner as in Example 1 to obtain a silicone polymer.

100 parts by weight of this silicone polymer and 350 parts by weight of dimethylpolysiloxane (viscosity at 25° C.: 6 cSt) were mixed and dispersed, and thoroughly kneaded by a triple roll mill under a shearing force to obtain a silicone composition. This composition was a homogeneous paste-like material, smooth to the touch and having a viscosity of 48,000 cP. 50 parts by weight of this paste-like silicone composition was mixed with 50 parts by weight of water. The water was easily dispersed by merely stirring the mixture to give a homogeneous creamy composition.

Example 11

100 g of organohydrogenpolysiloxane prepared in Synthetic Example, 74 g of ethanol, 79 g of polyoxyalkylene of the following formula (17), $$CH_2=CHCH_2O(C_2H_4O)_5(C_3H_6O)_5CH_2CH=CH_2 \qquad (17)$$

and 0.3 g of 3 wt % solution of chloroplatinic acid in ethanol were charged into a reaction vessel and processed in the same manner as in Example 1 to obtain silicone polymer particles.

100 parts by weight of this silicone polymer and 200 parts by weight of dimethylpolysiloxane (viscosity at 25° C.: 6 cSt) were mixed and dispersed, and thoroughly kneaded by a triple roll mill under a shearing force to swell the polymer, thus obtaining a silicone composition. This composition was a homogeneous paste-like material, smooth to the touch and having a viscosity of 43,000 cP. 50 parts by weight of this paste-like silicone composition was mixed with 50 parts by weight of water. The water was easily dispersed by merely stirring the mixture to give a homogeneous creamy composition.

Example 12

100 g of organohydrogenpolysiloxane prepared in Synthetic Example, 72 g of ethanol, 28.9 g of organopolysiloxane of the following formula (18),

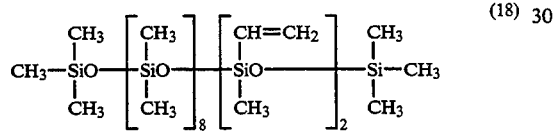

and 0.3 g of 3 wt % solution of chloroplatinic acid in ethanol were charged into a reaction vessel and processed in the same manner as in Example 1 to obtain silicone polymer particles.

100 parts by weight of this silicone polymer and 300 parts by weight of octamethyltrisiloxane (viscosity at 25° C.: 1 cSt) were mixed and dispersed, and thoroughly kneaded by a triple roll mill under a shearing force to swell the polymer, thus obtaining a silicone composition. This composition was a homogeneous paste-like material, smooth to the touch and having a viscosity of 55,000 cP. 50 parts by weight of the paste-like silicone composition was mixed with 50 parts by weight of water. The water was easily dispersed by merely stirring the mixture to give a homogeneous creamy composition.

Example 13

100 g of organohydrogenpolysiloxanes of which the average composition is shown by the compound of formula (10), used in Example 2, 103.0 g of ethanol, 23.6 g of polyoxyalkylene of which the average composition is shown by formula (11), used in Example 2, 82.4 g of 1,3-butylene glycol, and 0.3 g of 3 wt % solution of chloroplatinic acid in ethanol were charged into a reaction vessel and processed in the same manner as in Example 1 to obtain a silicone polymer.

100 parts by weight of this silicone polymer and 100 parts by weight of dimethylpolysiloxane (viscosity at 25° C.: 50 cSt) were mixed and dispersed, and thoroughly kneaded by a triple roll mill under a shearing force to swell the polymer, thus obtaining a silicone composition. This composition was a homogeneous paste-like material, smooth to the touch and having a viscosity of 65,000 cP. 50 parts by weight of this paste-like silicone composition was mixed with 50 parts by weight of water. The water was easily dispersed by merely stirring the mixture to give a homogeneous creamy composition.

Example 14

100 g of organohydrogenpolysiloxane of which the average composition is shown by the compound of the following formula (19),

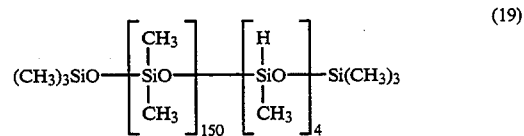

160 g of ethanol, 34.7 g of polyoxyalkylene of which the average composition is shown by the compound of the following formula (20),

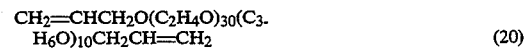

$$CH_2=CHCH_2O(C_2H_4O)_{30}(C_3H_6O)_{10}CH_2CH=CH_2 \qquad (20)$$

20 g of ethylene glycol, 13.7 g of dimethylpolysiloxane (viscosity at 25° C.: 10 cSt), and 0.3 g of 3 wt % solution of chloroplatinic acid in ethanol were charged into a reaction vessel and processed in the same manner as in Example 1 to obtain a silicone polymer.

100 parts by weight of this silicone polymer and 300 parts by weight of decamethylcyclopentasiloxane were mixed and dispersed, and thoroughly kneaded by a triple roll mill under a shearing force to obtain a swelled silicone composition. This composition was a homogeneous paste-like material, smooth to the touch and having a viscosity of 52,000 cP. 50 parts by weight of this paste-like silicone composition was mixed with 50 parts by weight of water. The water was easily dispersed by merely stirring the mixture to give a homogeneous creamy composition.

Reference Example 1

183 g (0.1 mol) of methylhydrogenpolysiloxane of which the average composition is shown by the compound of the following formula (21),

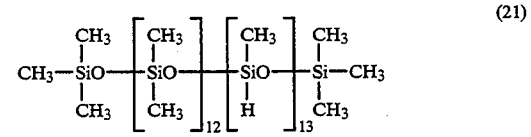

308 g (1 mol) of allyl oleyl ether, 136 g (0.3 mol) of allylated polyether of which the average composition is shown by the compound of the following formula (22), $$CH_2=CHCH_2O(C_2H_4O)_9H \qquad (22)$$

and 500 g of ethanol were weighed and placed in a 2l flask. After the addition of 2 g of chloroplatinic acid neutralized with chlorine (an ethanol solution, platinum concentration: 0.5%), the mixture was reacted for 5 hours under refluxing of ethanol. After the reaction, the solvent was evaporated and nonvolatile materials were removed by filtration to obtain 570 g of oily product of organopolysiloxane co-modified by polyoxyethylene oleyl ether, of which the average composition is shown by the compound of the following formula (23) (yield 91%).

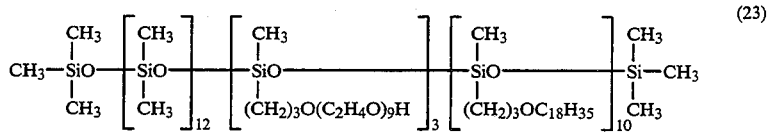
(23)

Reference Example 2

527 g of an oily product of organopolysiloxane co-modified by polyoxyethylene and myristyl ether, of which the average composition is shown by the compound of the following formula (24), was prepared in the same manner as in Reference Example 1, except that 254 g (1 mol) of allyl myristyl ether was used instead of 308 g (1 mol) of allyl oleyl ether (yield: 92%).

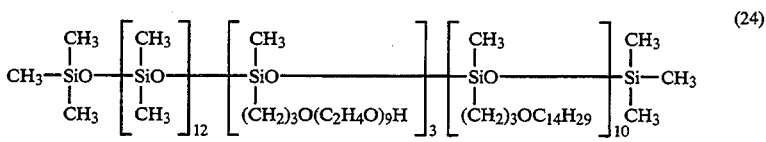
(24)

Reference Example 3

610 g of an oily product of organopolysiloxane co-modified by polyoxyethylene and isostearyl ether, of which the average composition is shown by the compound of the following formula (25) was prepared in the same manner as in Reference Example 1, except that 310 g (1 mol) of ally isostearyl ether was used instead of 308 g (1 mol) of allyl oleyl ether (yield: 97%).

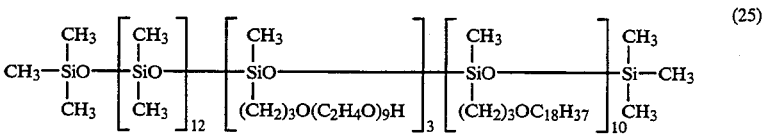
(25)

Example 15 <Face Cream>

| (Formulation) | % by weight |
|---|---|
| (1) Paste-like silicone composition prepared in Example 4 | 10 |
| (2) Octanoic triglyceride | 30 |
| (3) 1,3-Butylene glycol | 20 |
| (4) Purified water | Balance |
| (5) Perfume | q.s. |

(Method of preparation)
A. (1) and (2) were blended.
B. (3) and (4) were blended.
C. B was added to A while stirring and then (5) was added to the mixture.

A face cream obtained according to the above procedure could well spread and give a moistened sensation. It gave a fresh and excellent sensation upon use.

Example 16 <Foundation>

| (Formulation) | % by weight |
|---|---|
| (1) Paste-like silicone composition prepared in Example 4 | 8.0 |
| (2) Dimethylpolysiloxane (Viscosity at 25° C.: 6 cSt) | 2.0 |
| (3) Octanoic Triglyceride | 4.0 |
| (4) Diglycerol triisostearate | 6.0 |
| (5) Squalane | 8.0 |
| (6) Methylphenylpolysiloxane | 10.0 |
| (7) Titanium dioxide | 23.0 |
| (8) Mica | 14.0 |
| (9) Pigment | 5.0 |
| (10) Purified water | Balance |

(Method of preparation)
A. (1)–(6) were blended.
B. (7)–(9) were blended and pulverized to homogenize.
C. B was added to A and the mixture was kneaded with a triple roll mill, followed by the addition of (10) while stirring.

The foundation obtained according to the above procedure gave a fresh sensation upon use without stickiness. It spread excellently over the skin producing a homogeneous cosmetic film and exhibiting superior make-up retentivity.

Examples 17–18, Comparative Example 1 <W/O Type Creams>

W/O type creams with formulations shown in Table 1 were prepared according to the procedure outlined below. Their sensation upon use and stabilities over time were evaluated and rated according to the standard shown below. The results are shown in Table 1.

TABLE 1

| | % by weight | | |
|---|---|---|---|
| | Example | | Comparative |
| | 17 | 18 | Example 1 |
| (1) Paste-like silicone composition prepared in Example 4 | 10 | 10 | 10 |
| (2) Dimethylpolysiloxane (Viscosity at 25° C.: 6 cSt) | 5 | 5 | 5 |
| (3) Silicic acid anhydride (Aerosil 200) | 0.2 | — | — |
| (4) Hydrophobic silica | — | 0.2 | — |

TABLE 1-continued

| | % by weight | | |
|---|---|---|---|
| | Example | | Comparative |
| | 17 | 18 | Example 1 |
| (CAB-O-SIL TS-530) | | | |
| (5) 1,3-Butylene glycol | 10 | 10 | 10 |
| (6) Ethanol | 2 | 2 | 2 |
| (7) Preservative | q.s. | q.s. | q.s. |
| (8) Purified water | Balance | Balance | Balance |
| Stability over time (40° C.) | | | |
| After 1 month | AAA | AAA | BBB |
| After 3 months | AAA | AAA | BBB |
| Feeling upon use | | | |
| Freshness | AAA | AAA | AAA |
| Spreadability | AAA | AAA | AAA |

(Method of preparation)
A. (1)–(4) were blended.
B. (5)–(8) were heated and blended to homogenize.
C. B was added to A while stirring and the mixture was cooled.

(Evaluation standard)
Stability over time:
  AAA: Excellent with no change being observed
  BBB: Slightly gelled
  CCC: Slightly oozes liquid
  DDD: Oozes and separates liquid from solid
Feeling upon use
  AAA: Excellent
  BBB: Good
  CCC: Cannot ascertain good or bad
  DDD: Bad As can be seen from the above results, W/O type creams of Examples 17 and 18 exhibited superior stability over time, without losing the effects of the excellent sensation upon use provided by the paste-like silicone composition.

Example 19 <Creamy Eyeshadow>

| (Formulation) | % by weight |
|---|---|
| (1) Paste-like silicone composition prepared in Example 13 | 10 |
| (2) Dimethylpolysiloxane (Viscosity at 25° C.: 6 cSt) | 10 |
| (3) Octanoic triglyceride | 20 |
| (4) Hydrophobic silica (Aerosil R-972) | |
| (5) Titanated mica | 5 |
| (6) Iron oxide titanated mica | 5 |
| (7) Mica | 3 |
| (8) Colored pigment | 2 |
| (9) 1,3-Butylene glycol | 10 |
| (10) Preservative | q.s. |
| (11) Perfume | q.s. |
| (12) Purified water | Balance |

(Method of preparation)
A. (1)–(4) were blended and (5)–(8) were added to the blend to homogeneously disperse.
B. (9), (10) and (12) were mixed and heated to dissolve.
C. B was added to A and mixed with stirring, (11) was added to the mixture, and the whole mixture was cooled.

Example 20 <Sunscreen Cream>

| (Formulation) | % by weight |
|---|---|
| (1) Paste-like silicone composition prepared in Example 8 | 15 |
| (2) Methylphenylpolysiloxane | 5 |
| (3) Cetyl 2-ethylhexanoate | 5 |
| (4) Hydrophobic silica (CAB-O-SIL TS-530) | 0.5 |
| (5) UV Absorber | 5.5 |
| (6) Perfume | q.s. |
| (7) 1,3-Butylene glycol | 10 |
| (8) Preservative | q.s. |
| (9) Purified water | Balance |

(Method of preparation)
A. (3) and (5) were heated to dissolve, added to the mixture of (1), (2) and (4), and homogeneously blended.
B. (7)–(9) were mixed and heated to dissolve.
C. B was added to A and mixed with stirring, (6) was then added, and the mixture was cooled.

The water-in-oil type cosmetic compositions prepared in Examples 19 and 20 exhibited an excellent sensation upon use which is superior to any conventional cosmetic compositions. They were fresh giving no sticky sensation and very stable over time.

Examples 21–24, Comparative Example 2 <W/O Type Creams>

W/O type creams with formulations shown in Table 2 were prepared according to the procedure outlined below. Their sensation upon use and stabilities over time were evaluated and rated according to the standard shown below. The results are shown in Table 2.

TABLE 2

| | | % by weight | | | | |
|---|---|---|---|---|---|---|
| | | Example | | | | Comparative |
| | | (21) | (22) | (23) | (24) | Example 2 |
| (1) | Paste-like silicone composition prepared in Example 4 | 10 | 10 | 10 | 10 | 10 |
| (2) | Dimethylpolysiloxane (Viscosity at 25° C.: 6 cSt) | 5 | 5 | 5 | 5 | 5 |
| (3) | Octanoic triglyceride | 10 | 10 | 10 | 10 | 10 |
| (4) | Glycerol | 2 | 2 | 2 | 2 | 2 |
| (5) | 1,3-Butylene glycol | 10 | 10 | 10 | 10 | 10 |
| (6) | Maltose | 2 | — | — | 2 | — |
| (7) | Sorbitol (70% aqueous solution) | — | 5 | — | — | — |
| (8) | Sodium chloride | — | — | 1 | 1 | — |
| (9) | Preservative | q.s. | q.s. | q.s. | q.s. | q.s. |
| (10) | Purified water | Balance | Balance | Balance | Balance | Balance |
| Stability over time (after 4 weeks) | | | | | | |
| At 5° C. | | AAA | AAA | AAA | AAA | BBB |

TABLE 2-continued

|  | % by weight | | | | |
|---|---|---|---|---|---|
|  | Example | | | | Comparative |
|  | (21) | (22) | (23) | (24) | Example 2 |
| At room temperature | AAA | AAA | AAA | AAA | AAA |
| At 40° C. | AAA | AAA | AAA | AAA | BBB |
| Feeling upon use | | | | | |
| Freshness | BBB | BBB | AAA | BBB | AAA |
| Moistened sensation | AAA | AAA | BBB | AAA | BBB |
| Spreadability | AAA | AAA | AAA | AAA | AAA |

(Method of preparation)
  A. (1)–(3) were blended.
  B. (4)–(10) were heated and blended to homogenize.
  C. B was added to A while stirring and the mixture was cooled.

(Evaluation standard)
Stability over time (after 4 weeks):
  AAA: Excellent with no change being observed
  BBB: Slightly gelled
  CCC: Slightly oozes liquid
  DDD: Oozes and separates liquid
Feeling upon use
  AAA: Excellent
  BBB: Good
  CCC: Cannot ascertain good or bad
  DDD: Bad As can be seen from the above results, W/O type creams of Examples 21–24 exhibited superior stability over time, without losing the effects of the excellent sensation upon use provided by the paste-like silicone composition.

Example 25 <Creamy Foundation>

| (Formulation) | % by weight |
|---|---|
| (1) Paste-like silicone composition prepared in Example 8 | 15 |
| (2) Dimethylpolysiloxane (Viscosity at 25° C.: 6 cSt) | 5 |
| (3) Decamethylcyclopentasiloxane | 5 |
| (4) Octanoic triglyceride | 8 |
| (5) Silicone-treated powder* | 20 |
| (6) Maltose | 2 |
| (7) Sodium sulfate | 0.5 |
| (8) Preservative | q.s. |
| (9) Perfume | q.s. |
| (10) Purified water | Balance |

*Composition of silicone-treated powder
Titanium dioxide 40%
Mica 29%
Talc 20%
Red iron oxide 2%
Yellow iron oxide 6%
Black iron oxide 2%
Methylhydrogenpolysiloxane 1%

(Method of preparation)
  A. (5) was added to (1)–(4) to homogeneously disperse in (1)–(4).
  B. (6)–(8) and (10) were heated to dissolve.
  C. B was added to A and mixed with stirring, (9) was added to the mixture, and the resulting mixture was cooled.

Example 26 <Hand Cream>

| (Formulation) | % by weight |
|---|---|
| (1) Paste-like silicone composition prepared in Example 7 | 10 |
| (2) Methylphenylsiloxane | 5 |

-continued

| (Formulation) | % by weight |
|---|---|
| (3) Decamethylcyclopentasiloxane | 5 |
| (4) Perfume | q.s. |
| (5) Glycerol | 20 |
| (6) 1,3-Butylene glycol | 10 |
| (7) Sorbitol (70% aq. solution) | 5 |
| (8) Glucose | 2 |
| (9) Calcium carbonate | 1 |
| (10) Preservative | q.s. |
| (11) Purified water | Balance |

(Method of preparation)
  A. (1)–(3) were blended.
  B. (5)–(11) were heated to dissolve.
  C. B was added to A and mixed with stirring, (4) was added to the mixture, and the resulting mixture was cooled.

Example 27 <Creamy Rouge>

| (Formulation) | % by weight |
|---|---|
| (1) Paste-like silicone composition prepared in Example 13 | 8 |
| (2) Octanoic triglyceride | 3 |
| (3) Dimethylpolysiloxane (Viscosity at 25° C.: 6 cSt) | 3 |
| (4) Liquid paraffin | 2 |
| (5) Titanium dioxide | 3 |
| (6) Talc | 1 |
| (7) Titanated mica | 3 |
| (8) Red #226 | 0.2 |
| (9) Yellow iron oxide | 0.8 |
| (10) Glycerol | 5 |
| (11) 1,3-Butylene glycol | 10 |
| (12) Starch | 2 |
| (13) Preservative | q.s. |
| (14) Perfume | q.s. |
| (15) Purified water | Balance |

(Method of preparation)
  A. (1)–(4) were mixed and to the mixture was added a homogeneous blend of (5)–(9) to homogeneously disperse the latter into the former.
  B. (10)–(13) and (15) were heated to dissolve.
  C. B was added to A and mixed with stirring, (14) was added to the mixture, and the resulting mixture was then cooled.

Water-in-oil type cosmetic compositions prepared in Examples 25–27 exhibited an excellent sensation upon use which has not been experienced with conventional cosmetic compositions. They were well spreadable giving a moistened sensation upon use and were very stable over time.

Examples 28–30, Comparative Example 3 <W/O Type Creams>

W/O type creams with formulations shown in Table 3 were prepared according to the procedure outlined below. Their sensation upon use and stabilities over time were evaluated according to the standard shown below. In addition, their colors were observed and the diameter water drop in the systems were measured. The results are shown in Table 3.

TABLE 3

| | | % by weight | | |
| | | Example | | Comparative Example |
| | | 28 | 29 | 30 | 3 |
|---|---|---|---|---|---|
| (1) | Paste-like silicone composition prepared in Example 2 | 9 | 9 | 9 | — |
| (2) | Dimethylpolysiloxane (Viscosity at 25° C.: 6 cSt) | 20 | 6 | 6 | 29 |
| (3) | Octanoic triglyceride | 5 | 19 | 19 | 5 |
| (4) | Polyoxyalkylene-modified organopolysiloxane surfactant *1 | 2 | — | — | 2 |
| (5) | Polyoxyalkylene-modified organopolysiloxane surfactant *2 | — | 2 | — | — |
| (6) | Polyoxyalkylene-modified organopolysiloxane surfactant prepared in Reference Example 1 | — | — | 2 | — |
| (7) | Citric acid | 0.3 | 0.3 | 0.3 | 0.3 |
| (8) | Sodium citrate | 1.2 | 1.2 | 1.2 | 1.2 |
| (9) | 1,3-Butylene glycol | 5 | 5 | 5 | 5 |
| (10) | Preservative | q.s. | q.s. | q.s. | q.s. |
| (11) | Perfume | q.s. | q.s. | q.s. | q.s. |
| (12) | Purified water | Balance | Balance | Balance | Balance |
| Stability over time | | AAA | AAA | AAA | AAA |
| Feeling upon use | | | | | |
| Freshness | | AAA | AAA | BBB | BBB |
| Moistened sensation | | BBB | BBB | AAA | CCC |
| Smoothness upon application | | AAA | AAA | AAA | BBB |
| Color | | White | White | White | White |
| Diameter of water drops (μm) | | 1-4 | 1-4 | 1-4 | 1-4 |

*1 A compound of formula (4) with $R^6=R^8=R^9=CH_3$, $R^{10}=H$, p = 20–30, q = 2–5, r = 3, s = 2–5, t = 0
*2 A compound of formula (5) with $R^6=R^{12}=R^{13}=CH_3$, $R^{10}=H$, $R^{11}=C_{16}$ alkyl group, p = 20–60, q = 1–10, r = 3, s = 2–10, t = 2–10, t = 2, u = 2–20

(Method of preparation)
A. (7), (8) and a portion of (12) were slowly added to a mixture of (4)–(6) with stirring to obtain a gel-like composition.
B. (1)–(3) were mixed, A was added to the mixture and heated to 70° C.
C. (9), (10), and the remaining portion of (12) were mixed and heated to dissolve and kept at 70° C.
D. C was added to B to emulsify, followed by the addition of (11), and the mixture was cooled to obtain a water-in-oil type cream.

(Evaluation standard)
Stability over time:
The composition was allowed to stand in a thermostat at 50° C. to observe and evaluate the states of the compositions after 4 weeks.
AAA: Excellent with no change being observed
BBB: Slight separation was observed with formation of coagulation.
CCC: Separation was manifest with formation of coagulation.

Feeling upon use
AAA: Excellent
BBB: Good
CCC: Average
DDD: Bad

As can be seen from the results of Table 3, creams prepared in Examples 28–30 were very stable and exhibited a good sensation upon use. They were fine emulsions when their colors were white. The cream of Comparative Example 3 in which no paste-like silicone composition was used formed the same as creams of the present invention, but exhibited insufficient stability over time and an unsatisfactory sensation upon use.

Example 31 <Creamy Foundation>

| (Formulation) | % by weight |
|---|---|
| (1) Paste-like silicone composition prepared in Example 7 | 8.0 |
| (2) Dimethylpolysiloxane (Viscosity at 25° C.: 6 cSt) | 7.0 |
| (3) Octanoic triglyceride | 14.0 |
| (4) Diisooctanoic acid neopentyl glycol | 5.0 |
| (5) Jojoba oil | 2.0 |
| (6) Polyoxyalkylene-modified organopolysiloxane surfactant prepared in Reference Example 1 | 1.0 |
| (7) Titanium dioxide | 8.0 |
| (8) Colored pigment | 4.0 |
| (9) Mica | 3.0 |
| (10) Talc | 3.0 |
| (11) 1,3-Butylene glycol | 4.8 |
| (12) Preservative | q.s. |
| (13) Perfume | q.s. |
| (14) Purified water | Balance |

(Method of preparation)
A. (1)–(6) were mixed and (7)–(10) were added to the mixture to disperse homogeneously.
B. (11), (12) and (14) were heated to dissolve and added to A to emulsify. (13) was added to the resulting and the mixture was cooled.

The creamy foundations prepared by the above method were stable over time and provided an excellent Sensation upon use giving a fresh sensation without stickiness. They have excellent water repellency and exhibited a high make-up effect.

Example 32, Comparative Examples 4 and 5 <Creamy Foundations>

Creamy foundations with formulations shown in Table 4 were prepared according to the procedure outlined below. Their sensation upon use and stabilities over time were evaluated and rated according to the standard shown below. The results are shown in Table 4.

TABLE 4

| | | % by weight | | |
| | | Example | Comparative Example | |
| | | 32 | 4 | 5 |
|---|---|---|---|---|
| (1) | Starch fatty acid ester | 2 | 2 | 4 |
| (2) | Sucrose fatty acid ester | 2 | 2 | 5 |
| (3) | Octanoic triglyceride | 6 | 6 | 21 |
| (4) | Paste-like silicone composition prepared in Example 7 | 6 | — | — |
| (5) | Silicone gel composition *1 | — | 6 | 10 |
| (6) | Dimethylpolysiloxane (Viscosity at 25° C.: 6 cSt) | 9 | 9 | 25 |
| (7) | Carboxy vinyl polymer | 0.6 | 0.6 | 0.2 |
| (8) | Sodium hydroxide | 0.12 | 0.12 | 0.04 |
| (9) | Purified water | Balance | Balance | Balance |
| (10) | 1,3-Butylene glycol | 5 | 5 | 5 |
| (11) | Titanium dioxide | 7 | 7 | 7 |
| (12) | Inorganic pigment | 1.8 | 1.8 | 1.8 |

TABLE 4-continued

|  |  | % by weight | | |
|---|---|---|---|---|
|  |  | Example | Comparative Example | |
|  |  | 32 | 4 | 5 |
| (13) | Mica | 0.8 | 0.8 | 0.8 |
| (14) | Lecithin | 0.2 | 0.2 | 0.2 |
| (15) | Perfume | q.s. | q.s. | q.s. |
| (16) | Preservative | q.s. | q.s. | q.s. |
| Stability | | AAA | CCC | AAA |
| Feeling upon use | | AAA | — | BBB |

*1 Preparation of the silicone gel composition 1,790 g of dimethylhydrogenpolysiloxane of which the terminals were sealed by trimethylsilyl groups (average molecular weight: 2,340, Si—H 4.5 mol%) and 710 g of dimethylpolysiloxane of which the terminals were sealed by dimethyvinyllsilyl groups (average molecular weight: 930, vinyl group 7.7 mol%) were charged into a planetary mixer with an internal volume of 5 l and stirred to mix. After the addition of 0.5 g of a 2% solution of chloroplatinic acid in isopropanol, the temperature was raised to 70–80° C. and the stirring was continued for 2 hours. The internal pressure was reduced to 5–10 mm Hg to perform stripping for 30 minutes, thus obtaining a partially crosslinked organopolysiloxane polymer as a colorless, flexible solid material.

100 parts by weight of dimethylpolysiloxane having a viscosity of 6 cS at 25° C. was dispersed in 100 parts by weight of this organopolysiloxane polymer and thoroughly kneaded to swell, thus obtaining a silicone gel composition.

(Method of preparation)
A. (1)–(3) were mixed and heated to dissolve.
B. (7)–(10) and (16) were mixed and dissolved.
C. (11)–(15) were blended homogeneously and pulverized.
D. (4)–(6) were mixed and B was added to the mixture.
E. C and D were added to A and the mixture was homogenized to obtain a creamy foundation.

(Evaluation standard)
Stability over time (after 4 weeks):
AAA: Excellent with no change being observed
BBB: Slight separation was observed
CCC: Separation was manifest
Sensation upon use
AAA: clarifying and cool
BBB: Not clarifying and cool, but refreshing
CCC: Sensation is oily with no refreshness As can be seen from the results shown in Table 4, W/O type creamy foundation of Example 32 was very stable in spite of its high content of water and exhibited a fresh, clarifying and cool sensation which could not be afforded by conventional cosmetic compositions. In contrast, the foundation of Comparative Example 5, in which a silicone gel composition comprising a partially crosslinked organopolysiloxane polymer instead of the paste-like silicone composition of the present invention was used, provided no fresh, clarifying and cool sensation as exhibited by the foundation of the present invention, even though it was stable and gave a comparatively refreshing sensation without oiliness or stickiness. The stability of was damaged and the product became unusable with an increase of the water,amount (Comparative Example 4).

Obviously, numerous modifications and variations of the present invention are possible in light of the above teachings. It is therefore to be understood that within the scope of the appended claims, the invention may be practiced otherwise than as specifically described herein.

What is claimed is:
1. A water-in-oil cosmetic composition comprising:
(a) an oil phase component which comprises (i) a pasty silicone composition which can disperse water and (ii) silicic acid anhydride or hydrophobic silica, or both; and
(b) at least one water phase component comprising water and water soluble components;
wherein the pasty like silicone composition is prepared by kneading 100 parts by weight of a silicone polymer and 5 to 1,000 parts by weight of a silicone oil under a sufficient shearing force to produce a smooth and homogeneous outward appearance, and
wherein the silicone polymer is prepared by the addition polymerization of the following components (I) and (II):
(I) an organohydrogenpolysiloxane represented by the following formula (1),

$$R^1{}_a R^2{}_b H_c SiO_{(4-a-b-c)/2} \qquad (1)$$

wherein
$R^1$ represents a substituted or unsubstituted alkyl, aryl, or aralkyl group having 1 to 18 carbon atoms, or a halogenated hydrocarbon group;
$R^2$ represents a group,

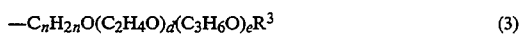

$$-C_n H_{2n} O(C_2 H_4 O)_d (C_3 H_6 O)_e R^3 \qquad (3)$$

wherein
$R^3$ is a hydrogen, a saturated aliphatic hydrocarbon group having 1 to 10 carbon atoms, or a group —(CO)—$R^5$, wherein $R^5$ is a saturated aliphatic hydrocarbon group having 1 to 5 carbon atoms,
d is an integer of 2 to 200, and
e is an integer of 0 to 200,
provided that d+e is 3 to 200, and n is 2 to 6;
a is a value satisfying inequality $1.0 \leq a \leq 2.5$;
b is a value satisfying inequality $0.001 \leq b \leq 1.0$; and
c is a value satisfying inequality $0.001 \leq c \leq 1.0$;
or an organohydrogenpolysiloxane represented by the following formula (2),

$$R^1{}_f H_g SiO_{(4-f-g)/2} \qquad (2)$$

wherein
$R^1$ is the same as defined in formula (1),
f is a value satisfying inequality $1.0 \leq f \leq 3.0$,
g is a value satisfying inequality $0.001 \leq g \leq 1.5$;
or a mixture of said organohydrogenpolysiloxanes of formulas (1) and (2), and
(II) a polyoxyalkylene represented by the following formula (A),

$$C_m H_{2m-1} O(C_2 H_4 O)_h (C_3 H_6 O)_i C_m H_{2m-1} \qquad (A)$$

wherein
h is an integer of 2 to 200,
i is an integer of 0 to 200, provided that h+i is 3 to 200, and
m is 2 to 6,
or an organopolysiloxane represented by the following formula (B), $$R^1_j R^4_k SiO_{(4-j-k)/2} \quad (B)$$

wherein
R¹ is the same as defined in formula (1),
R₄ is a monovalent hydrocarbon group having an aliphatic unsaturated bond at the terminal thereof and containing 2 to 10 carbon atoms,
j is a value satisfying inequality $1.0 \leq j \leq 3.0$, and
k is a value satisfying inequality $0.001 \leq k \leq 1.5$,
or a mixture of the polyoxyalkylene of formula (A) and the organopolysiloxane of formula (B),
wherein at least one organohydrogenpolysiloxane of formula (1) or at least one polyoxyalkylene of formula (A) is contained as an essential component of the addition polymerization.

2. A water-in-oil cosmetic composition as claimed in claim 1, comprising from 0.01 to 10% of the oil phase components of said silicic acid anhydride or hydrophobic silica.

3. A water-in-oil cosmetic composition as claimed in claim 2 wherein the hydrophobic silica is trimethylsiloxylated silica, dimethylsiloxylated silica, octylsiloxylated silica or silicone oil treated silica.

4. A water-in-oil cosmetic composition comprising:
(a) an oil phase component which comprises (i) a pasty silicone composition which can disperse water; and (ii) silicic acid anhydride or hydrophobic silica, or both; and
(b) at least one water phase component comprising water and water soluble components;
wherein the pasty silicone composition is prepared by kneading 100 parts by weight of a silicone polymer and 5 to 1,000 parts by weight of a silicone oil under a sufficient shearing force to produce a smooth and homogeneous outward appearance, and wherein the silicone polymer is prepared by the addition polymerization, in the presence of 3 to 200 parts by weight of a low viscosity silicone oil having a viscosity of 100 cS or lower at 25° C. or a polyhydric alcohol, or both, of 100 parts by weight of components comprising,
(I) an organohydrogenpolysiloxane represented by the following formula (1), $$R^1_a R^2_b H_c SiO_{(4-a-b-c)/2} \quad (1)$$

wherein
R¹ represents a substituted or unsubstituted alkyl, aryl, or aralkyl group having 1 to 18 carbon atoms, or a halogenated hydrocarbon group;
R² represents a group $-C_n H_{2n} O(C_2 H_4 O)_d (C_3 H_6 O)_e R^3$
wherein
R³ is a hydrogen, a saturated aliphatic hydrocarbon group having 1 to 10 carbon atoms, or a group —(CO)—R⁵, wherein R⁵ is a saturated aliphatic hydrocarbon group having 1 to 5 carbon atoms,
d is an integer of 2 to 200,
e is an integer of 0 to 200,
provided that d+e is 2 to 200, and
n is 2 to 6;
a is a value satisfying inequality $1.0 \leq a \leq 2.5$;
b is a value satisfying inequality $0.001 \leq b \leq 1.0$; and
c is a value satisfying inequality $0.001 \leq c \leq 1.0$;
or an organohydrogenpolysiloxane represented by the following formula (2), $$R^1_f H_g SiO_{(4-f-g)/2} \quad (2)$$

wherein
R¹ is the same as defined in formula (1),
f is a value satisfying inequality $1.0 \leq f \leq 3.0$, and
g is a value satisfying inequality $0.001 \leq g \leq 1.5$;
or a mixture of said organohydrogenpolysiloxanes of formulas (1) and (2); and
(II) a polyoxyalkylene represented by the following formula (A)

$$C_m H_{2m-1} O(C_2 H_4 O)_h (C_3 H_6 O)_i C_m H_{2m-1} \quad (A)$$

wherein
h is an integer of 2 to 200,
i is an integer of 0 to 200,
provided that h+i is 2 to 200, and
m is 2 to 6,
or an organopolysiloxane represented by the following formula (B), $$R^1_j R^4_k SiO_{(4-j-k)/2} \quad (B)$$

wherein
R¹ is the same as defined in formula (1),
R⁴ is a monovalent hydrocarbon group having an aliphatic unsaturated bond at the terminal thereof and containing 2 to 10 carbon atoms,
j is a value satisfying inequality $1.0 \leq j \leq 3.0$, and
k is a value satisfying inequality $0.001 \leq k \leq 1.5$,
or a mixture of the polyoxyalkylene of formula (A) and the organopolysiloxane of formula (B),
wherein at least one organohydrogenpolysiloxane of formula (1) or at least one polyoxyalkylene of formula (A) are contained as an essential component of the addition polymerization.

5. A water-in-oil cosmetic composition as claimed in claim 4 comprising from 0.01 to 10% in the oil phase components of said silica acid anhydride or hydrophobic silica.

6. A water-in-oil cosmetic composition as claimed in claim 5 wherein the hydrophobic silica is trimethylsiloxylated silica, dimethylsiloxylated silica, octylsiloxylated silica or silicone oil treated silica.

7. A water-in-oil cosmetic composition comprising:
(a) an oil phase component which comprises a pasty silicone composition which can disperse water; and
(b) water and a stabilizing effective amount of one or more components selected from the group consisting of saccharides, sugar alcohols, and inorganic salts, as water phase components;
wherein the pasty silicone composition is prepared by kneading 1 00 parts by weight of a silicone polymer and 5 to 1,000 parts by weight of a silicone oil under sufficient shearing force to produce a smooth and homogeneous outward appearance, and
wherein the silicone polymer is prepared by the addition polymerization of the following components (I) and (II):
(I) an organohydrogenpolysiloxane represented by the following formula (1), $$R^1_a R^2_b H_c SiO_{(4-a-b-c)/2} \quad (1)$$

wherein $R^1$ represents a substituted or unsubstituted alkyl, aryl, or aralkyl group having 1 to 18 carbon atoms, or a halogenated hydrocarbon group;

$R_2$ represents a group, $$-C_nH_{2n}O(C_2H_4O)_d(C_3H_6O)_eR^3 \qquad (3)$$

wherein $R^3$ is a hydrogen, a saturated aliphatic hydrocarbon group having 1 to 10 carbon atoms, or a group —(CO)—$R^5$, wherein $R^5$ is a saturated aliphatic hydrocarbon group having 1 to 5 carbon atoms, d is an integer of 2 to 200, and e is an integer of 0 to 200, provided that d+e is 3 to 200, and n is 2 to 6;

a is a value satisfying inequality $1.0 \leq a \leq 2.5$;

b is a value satisfying inequality $0.001 \leq b \leq 1.0$; and c is a value satisfying inequality $0.001 \leq c \leq 1.0$;

or an organohydrogenpolysiloxane represented by the following formula (2), $$R^1_f H_g SiO_{(4-f-g)/2} \qquad (2)$$

wherein $R^1$ is the same as defined in formula (1), f is a value satisfying inequality $1.0 \leq f \leq 3.0$, g is a value satisfying inequality $0.001 \leq g \leq 1.5$;

or a mixture of said organohydrogenpolysiloxanes of formulas (1) and (2), and (II) a polyoxyalkylene represented by the following formula (A), $$C_mH_{2m-1}O(C_2H_4O)_h(C_3H_6O)_iC_mH_{2m-1} \qquad (A)$$

wherein h is an integer of 2 to 200, i is an integer of 0 to 200, provided that h+i is 3 to 200, and m is 2 to 6, or an organopolysiloxane represented by the following formula (B), $$R^1_j R^4_k SiO_{(4-j-k)/2} \qquad (B)$$

wherein $R^1$ is the same as defined in formula (1), $R^4$ is a monovalent hydrocarbon group having an aliphatic unsaturated bond at the terminal thereof and containing 2 to 10 carbon atoms, j is a value satisfying inequality $1.0 \leq j \leq 3.0$, and k is a value satisfying inequality $0.001 \leq k \leq 1.5$, or a mixture of the polyoxyalkylene of formula (A) and the organopolysiloxane of formula (B), wherein at least one organohydrogenpolysiloxane of formula (1) or at least one polyoxyalkylene of formula (A) is contained as an essential component of the addition polymerization.

8. A water-in-oil cosmetic composition as claimed in claim 7 wherein the water phase component is glucose, fructose, galactose, xylose, maltose, sucrose, lactose, starch, dextrin, sorbitol, mannitol, maltitol, an inorganic salt selected from the group consisting of sodium, potassium, calcium, magnesium, and aluminum, or a zinc salt of hydrochloric acid, sulfuric acid, carbonic acid or nitric acid.

9. A water-in-oil cosmetic composition as claimed in claim 8 wherein the stabilizing effective amount is from 0.1 to 20% of the total amount of the oil phase components.

10. A water-in-oil cosmetic composition comprising:

(a) an oil phase component which comprises a pasty silicone composition which can disperse water; and (b) water and one or more components selected from the group consisting of saccharides, sugar alcohols, and inorganic salts, as water phase components;

wherein the pasty silicone composition is prepared by kneading 100 parts by weight of a silicone polymer and 5 to 1,000 parts by weight of a silicone oil under sufficient shearing force to produce a smooth and homogeneous outward appearance, and wherein the silicone polymer is prepared by the addition polymerization, in the presence of 3 to 200 parts by weight of a low viscosity silicone oil having a viscosity of 100 cS or lower at 25° C. or a polyhydric alcohol, or both, of 100 parts by weight of components comprising, (I) an organohydrogenpolysiloxane represented by the following formula (1), $$R^1_a R^2_b H_c SiO_{(4-a-b-c)/2} \qquad (1)$$

wherein $R^1$ represents a substituted or unsubstituted alkyl, aryl, or aralkyl group having 1 to 18 carbon atoms, or a halogenated hydrocarbon group;

$R^2$ represents a group —$C_nH_{2n}O(C_2H_4O)_d(C_3H_6O)_eR^3$ wherein $R^3$ is a hydrogen, a saturated aliphatic hydrocarbon group having 1 to 10 carbon atoms, or a group —(CO)—$R^5$, wherein $R^5$ is a saturated aliphatic hydrocarbon group having 1 to 5 carbon atoms, d is an integer of 2 to 200, e is an integer of 0 to 200, provided that d+e is 2 to 200, and n is 2 to 6;

a is a value satisfying inequality $1.0 \leq a \leq 2.5$;

b is a value satisfying inequality $0.001 \leq b \leq 1.0$; and c is a value satisfying inequality $0.001 \leq c \leq 1.0$;

or an organohydrogenpolysiloxane represented by the following formula (2), $$R^1_f H_g SiO_{(4-f-g)/2} \qquad (2)$$

wherein $R^1$ is the same as defined in formula (1), f is a value satisfying inequality $1.0 \leq f \leq 3.0$, and g is a value satisfying inequality $0.001 \leq g \leq 1.5$;

or a mixture of said organohydrogenpolysiloxanes of formulas (1) and (2), and (II) a polyoxyalkylene represented by the following formula (A)

$$C_mH_{2m-1}O(C_2H_4O)_h(C_3H_6O)_iC_mH_{2m-1} \qquad (A)$$

wherein h is an integer of 2 to 200, i is an integer of 0 to 200, provided that h+i is 2 to 200, and m is 2 to 6, or an organopolysiloxane represented by the following formula (B), $R^1{}_jR^4{}_kSiO_{(4-j-k)/2}$ (B)

wherein
$R^1$ is the same as defined in formula (1),
$R^4$ is a monovalent hydrocarbon group having an aliphatic unsaturated bond at the terminal thereof and containing 2 to 10 carbon atoms,
j is a value satisfying inequality $1.0 \leq j \leq 3.0$, and
k is a value satisfying inequality $0.001 \leq k \leq 1.5$,
or a mixture of the polyoxyalkylene of formula (A) and the organopolysiloxane of formula (B),
wherein at least one organohydrogenpolysiloxane of formula (1) or at least one polyoxyalkylene of formula (A) are contained as an essential component of the addition polymerization.

11. A water-in-oil cosmetic composition as claimed in claim 10 wherein the water phase component is glucose, fructose, galactose, xylose, maltose, sucrose, lactose, starch, dextrin, sorbitol, mannitol, maltitol, an inorganic salt selected from the group consisting of sodium, potassium, calcium, magnesium, and aluminum, or a zinc salt of hydrochloric acid, sulfuric acid, carbonic acid or nitric acid.

12. A water-in-oil cosmetic composition as claimed in claim 11 wherein the stabilizing effective amount is from 0.1 to 20% of the total amount of the oil phase components.

13. A water-in-oil cosmetic composition comprising:
(a) an oil phase component which comprises a pasty silicone composition which can disperse water;
(b) at least one water phase component comprising water and water soluble components; and a polyoxyalkylene-modified organopolysiloxane surface active agent
wherein the pasty silicone composition is prepared by kneading 100 parts by weight of a silicone polymer and 5 to 1,000 parts by weight of a silicone oil under sufficient shearing force to produce a smooth and homogenous outward appearance, and
wherein the silicone polymer is prepared by the addition polymerization of the following components (I) and (II):
(I) an organohydrogenpolysiloxane represented by the following formula (1), $R^1{}_aR^2{}_bH_cSiO_{(4-a-b-c)/2}$ (1)

wherein
$R^1$ represents a substituted or unsubstituted alkyl, aryl, or aralkyl group having 1 to 18 carbon atoms, or a halogenated hydrocarbon group;
$R^2$ represents a group, $-C_nH_{2n}O(C_2H_4O)_d(C_3H_6O)_eR^3$ (3)

wherein
$R^3$ is a hydrogen, a saturated aliphatic hydrocarbon group having 1 to 10 carbon atoms, or a group $-(CO)-R^5$, wherein $R^5$ is a saturated aliphatic hydrocarbon group having 1 to 5 carbon atoms,
d is an integer of 2 to 200, and
e is an integer of 0 to 200,
provided that d+e is 3 to 200, and n is 2 to 6;
a is a value satisfying inequality $1.0 \leq a \leq 2.5$;
b is a value satisfying inequality $0.001 \leq b \leq 1.0$; and
c is a value satisfying inequality $0.001 \leq c \leq 1.0$;

or an organohydrogenpolysiloxane represented by the following formula (2), $R^1{}_fH_gSiO_{(4-f-g)/2}$ (2)

wherein
$R^1$ is the same as defined in formula (1),
f is a value satisfying inequality $1.0 \leq f \leq 3.0$,
g is a value satisfying inequality $0.001 \leq g \leq 1.5$;
or a mixture of said organohydrogenpolysiloxanes of formulas (1) and (2), and
(II) a polyoxyalkylene represented by the following formula (A), $C_mH_{2m-1}O(C_2H_4O)_h(C_3H_6O)_iC_mH_{2m-1}$ (A)

wherein
h is an integer of 2 to 200,
i is an integer of 0 to 200, provided that h+i is 3 to 200, and
m is 2 to 6,
or an organopolysiloxane represented by the following formula (B), $R^1{}_jR^4{}_kSiO_{(4-j-k)/2}$ (B)

wherein
$R^1$ is the same as defined in formula (1),
$R^4$ is a monovalent hydrocarbon group having an aliphatic unsaturated bond at the terminal thereof and containing 2 to 10 carbon atoms,
j is a value satisfying inequality $1.0 \leq j \leq 3.0$, and
k is a value satisfying inequality $0.001 \leq k \leq 1.5$,
or a mixture of the polyoxyalkylene of formula (A) and the organopolysiloxane of formula (B),
wherein at least one organohydrogenpolysiloxane of formula (1) or at least one polyoxyalkylene of formula (A) is contained as an essential component of the addition polymerization.

14. A water-in-oil cosmetic composition as claimed in claim 13, wherein the polyoxyalkylene-modified organopolysiloxane surfactant is:
a compound of formula (4):

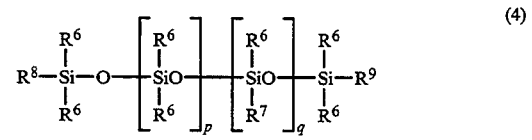

(4)

wherein:
$R^6$ represents an alkyl group having 1–5 carbon atoms or a phenyl group;
$R^7$ is a group $-(CH_2)_r-O-(C_2H_4O)_s-(C_3H_6O)_tR^{10}$
wherein $R^{10}$ is hydrogen or an alkyl group having from 1 to 5 carbon atoms; r is a number from 1 to 5; s is a number from 1–50; and t is a number from 0–30;
$R^8$ and $R^9$ are the same as either $R^6$ or $R^7$;
is a number from 5 to 300; and
q is a number from 0 to 50, provided that when q is 0, at least one of $R^8$ and $R^9$ is the same as $R^7$ and provided further that not all $R^6$s can be phenyl groups;
a compound of formula (5):

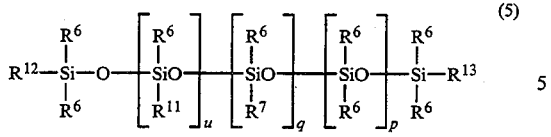

(5)

wherein:
R$^6$, R$^7$, p and q are the same as defined above;
R$^{11}$ is an alkyl group having 2-20 carbon atoms;
R$^{12}$ and R$^{13}$ are the same as at least one of R$^6$, R$^7$ and R$^{11}$; and
u is a number from 1 to 30, provided that when q is 0, at least one of R$^{12}$ and R$^{13}$ is the same as R$^7$, and further that not all R$^6$s can be phenyl groups;
or
a compound of formula (6):

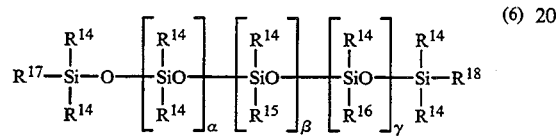

(6)

wherein:
R$^{14}$ represents an alkyl group having from 1 to 4 carbon atoms;
R$^{15}$ is a group —Q$^1$—O—(C$_2$H$_4$O)—(C$_3$H$_6$O)$_y$—R$^{19}$
  wherein Q$^1$ is a hydrocarbon group having 1 to 4 carbon atoms; R$^{19}$ is a hydrogen, an alkyl group having 1 to 4 carbon atoms, or an acetyl group; x is an integer of 1 or more; and y is an integer of 0 or more;
R$^{16}$ is a group —Q$_2$—O—R$^{20}$
  wherein Q$^2$ is a hydrocarbon group having 1 to 4 carbon atoms; and
  R$^{20}$ is a hydrocarbon group having 8 to 30 carbon atoms;
R$^{17}$ and R$^{18}$ are the same as at least one of R$^{14}$, R$^{15}$ or R$^{16}$;
α is an integer of 0 or more; and
β and γ are integers of 1 or more.

15. A water-in-oil composition as claimed in claim 14 wherein the amount of surfactant is from 0.01 to 10%.

16. A water-in-oil cosmetic composition comprising:
(a) an oil phase component which comprises a pasty silicone composition which can disperse water; and
(b) at least one water phase component comprising water and water soluble compounds; and
a polyoxyalkylene-modified organopolysiloxane surface active;
wherein the pasty silicone composition is prepared by kneading 100 parts by weight of a silicone polymer and 5 to 1,000 parts by weight of a silicone oil under sufficient shearing force to a smooth and homogeneous outward appearance, and
wherein the silicone polymer is prepared by the addition polymerization, in the presence of 3 to 200 parts by weight of a low viscosity silicone oil having a viscosity of 100 cS or lower at 25° C. or a polyhydric alcohol, or both, of 100 parts by weight of components comprising,
(I) an organohydrogenpolysiloxane represented by the following formula (1), $$R^1{}_aR^2{}_bH_cSiO_{(4-b-c)/2} \quad (1)$$

wherein
R$^1$ represents a substituted or unsubstituted alkyl, aryl, or aralkyl group having 1 to 18 carbon atoms, or a halogenated hydrocarbon group; R$^2$ represents a group —C$_n$H$_{2n}$O(C$_2$H$_4$O)$_d$(C$_3$H$_6$O)$_e$R$^3$
wherein
R$^3$ is a hydrogen, a saturated aliphatic hydrocarbon group having 1 to 10 carbon atoms, or a group —(CO)—R$^5$, wherein R$^5$ is a saturated aliphatic hydrocarbon group having 1 to 5 carbon atoms,
d is an integer of 2 to 200,
e is an integer of 0 to 200,
provided that d+e is 2 to 200, and
n is 2 to 6;
a is a value satisfying inequality 1.0≦a≦2.5;
b is a value satisfying inequality 0.001≦b≦1.0; and
c is a value satisfying inequality 0.001≦c≦1.0;
or an organohydrogenpolysiloxane represented by the following formula (2), $$R^1{}_fH_gSiO_{(4-f-g)/2} \quad (2)$$

wherein
R$^1$ is the same as defined in formula (1),
f is a value satisfying inequality 1.0≦f≦3.0, and
g is a value satisfying inequality 0.001≦g≦1.5;
or a mixture of said organohydrogenpolysiloxanes of formulas (1) and (2); and
(II) a polyoxyalkylene represented by the following formula (A)

$$C_mH_{2m-1}O(C_2H_4O)_h(C_3H_6O)_iC_mH_{2m-1} \quad (A)$$

wherein
h is an integer of 2 to 200,
i is an integer of 0 to 200,
provided that h+i is 2 to 200, and
m is 2 to 6,
or an organopolysiloxane represented by the following formula (B), $$R^1{}_jR^4{}_kSiO_{(4-j-k)/2} \quad (B)$$

wherein
R$^1$ is the same as defined in formula (1),
R$^4$ is a monovalent hydrocarbon group having an aliphatic unsaturated bond at the terminal thereof and containing 2 to 10 carbon atoms,
j is a value satisfying inequality 1.0≦j≦3.0, and
k is a value satisfying inequality 0.001≦k≦1.5,
or a mixture of the polyoxyalkylene of formula (A) and the organopolysiloxane of formula (B),
wherein at least one organohydrogenpolysiloxane of formula (1) or at least one polyoxyalkylene of formula (A) are contained as an essential component of the addition polymerization.

17. A water-in-oil cosmetic composition as claimed in claim 16, wherein the polyoxyalkylene-modified organopolysiloxane surfactant is:
a compound of formula (4):

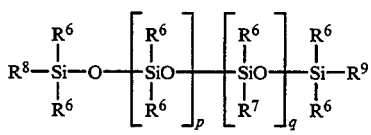
(4)

wherein:

$R^6$ represents an alkyl group having 1-5 carbon atoms or a phenyl group;

$R^7$ is a group $-(CH_2)_r-O-(C_2H_4O)_s-(C_3H_6O)_t-R^{10}$
wherein $R^{10}$ is hydrogen or an alkyl group having from 1-5 carbon atoms; r is a number from 1 to 5; s is a number from 1-50; and t is a number from 0-30;

$R^8$ and $R^9$ are the same as either $R^6$ or $R^7$;

p is a number from 5 to 300; and q is a number from 0 to 50, provided that when q is 0, at least one of $R^8$ and $R^9$ is the same as $R^7$ and provided further that not all $R^6$s can be phenyl groups;

a compound of formula (5):

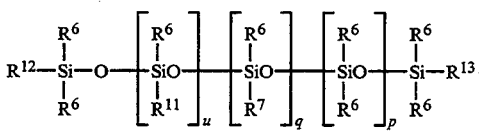
(5)

wherein:

$R^6$, $R^7$, p and q are the same as defined above;

$R^{11}$ is an alkyl group having 2-20 carbon atoms;

$R^{12}$ and $R^{13}$ are the same as at least one of $R^6$, $R^7$ and $R^{11}$; and u is a number from 1 to 30, provided that when q is 0, at least one of $R^{12}$ and $R^{13}$ is the same as $R^7$, and further that not all $R^6$s can be phenyl groups; or a compound of formula (6):

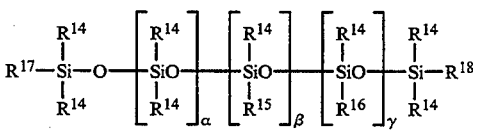
(6)

wherein:

$R^{14}$ represents an alkyl group having from 1 to 4 carbon atoms;

$R^{15}$ is a group $-Q^1-O-(C_2H_4O)_x-(C_3H_6O)_y-R^{19}$
wherein $Q^1$ is a hydrocarbon group having 1 to 4 carbon atoms; $R^{19}$ is a hydrogen, an alkyl group having 1 to 4 carbon atoms, or an acetyl group; x is an integer of 1 or more; and y is an integer of 0 or more;

$R^{16}$ is a group $-Q^2-O-R^{20}$
wherein $Q^2$ is a hydrocarbon group having 1 to 4 carbon atoms; and $R^{20}$ is a hydrocarbon group having 8 to 30 carbon atoms;

$R^{17}$ and $R^{18}$ are the same as at least one of $R^{14}$, $R^{15}$ or $R^{16}$;

$\alpha$ is an integer of 0 or more; and $\beta$ and $\gamma$ are integers of 1 or more.

18. A water-in-oil composition as claimed in claim 17 wherein the amount of surfactant is from 0.01 to 10%.

19. A water-in-oil type make-up cosmetic composition comprising:
(a) a semisolid oil or a liquid oil, or both,
(b) a solid oil or an oil gelling agent, or both,
(c) A water-in-oil type cosmetic composition comprising:
(a) an oil phase component which comprises a pasty silicone composition which can disperse water; and
(b) at least one water phase component;
wherein the pasty silicone composition is prepared by kneading 100 parts by weight of a silicone polymer and 5 to 1,000 parts by weight of a silicone oil under a sufficient shearing force to produce a smooth and homogenous outward appearance, and
wherein the silicone polymer is prepared by the addition polymerization of the following components (I) and (II):
(I) an organohydrogenpolysiloxane represented by the following formula (1),

(1)

wherein $R^1$ represents a substituted or unsubstituted alkyl, aryl, or aralkyl group having 1 to 18 carbon atoms, or a halogenated hydrocarbon group;

$R^2$ represents a group,

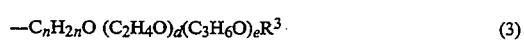
(3)

wherein $R^3$ is a hydrogen, a saturated aliphatic hydrocarbon group having 1 to 10 carbon atoms, or a group $-(CO)-R^5$, wherein $R^5$ is a saturated aliphatic hydrocarbon group having 1 to 5 carbon atoms, d is an integer of 2 to 200, and e is an integer of 0 to 200, provided that d+e is 3 to 200, and n is 2 to 6;

a is a value satisfying inequality $1.0 \leq a \leq 2.5$;

b is a value satisfying inequality $0.001 \leq b \leq 1.0$; and c is a value satisfying inequality $0.001 \leq c 1.0$;

or an organohydrogenpolysiloxane represented by the following formula (2),

(2)

wherein $R^1$ is the same as defined in formula (1), f is a value satisfying inequality $1.0 \leq f \leq 3.0$, g is a value satisfying inequality $0.001 \leq g \leq 1.5$;

or a mixture of said organohydrogenpolysiloxanes of formulas (1) and (2), and (II) a polyoxyalkylene represented by the following formula (A),

(A)

wherein h is an integer of 2 to 200, i is an integer of 0 to 200, provided that h+i is 3 to 200, and m is 2 to 6, or an organopolysiloxane represented by the following formula (B),

(B)

wherein $R^1$ is the same as defined in formula (1), $R^4$ is a monovalent hydrocarbon group having an aliphatic unsaturated bond at the terminal thereof and containing 2 to 10 carbon atoms, j is a value satisfying inequality $1.0 \leq j \leq 3.0$, and k is a value satisfying inequality $0.001 \leq k \leq 1.5$, or a mixture of the polyoxyalkylene of formula (A) and the organopolysiloxane of formula (B), wherein at least one organohydrogenpolysiloxane of formula (1) or at least one polyoxyalkylene of formula (A) is contained as an essential component of the addition polymerization (d) at least one water phase component comprising water and water soluble components; and (e) a cosmetic powder.

20. A water-in-oil make-up cosmetic composition comprising:

(a) a semisolid oil or a liquid oil, or both, (b) a solid oil or an oil gelling agent, or both, (c) a water-in-oil cosmetic composition comprising:

(a) an oil phase component which comprises a pasty silicone composition which can disperse water; and (b) at least one water phase component comprising water and water soluble components;

wherein the pasty silicone composition is prepared by kneading 100 parts by weight of a silicone polymer and 5 to 1,000 parts by weight of a silicone oil under a sufficient shearing force to produce a smooth and homogenous outward appearance, and wherein the silicone polymer is prepared by the addition polymerization, in the presence of 3 to 200 parts by weight of a low viscosity silicone oil having a viscosity of 100 cS or lower at 25° C. or a polyhydric alcohol, or both, of 100 parts by weight of components comprising, (I) an organohydrogenpolysiloxane represented by the following formula (1),

   (1)

wherein $R^1$ represents a substituted or unsubstituted alkyl, aryl, or aralkyl group having 1 to 18 carbon atoms, or a halogenated hydrocarbon group;

$R^2$ represents a group $-C_nH_{2n}O(C_2H_4O)_d(C_3H_6O)_eR^3$ wherein $R^3$ is a hydrogen, a saturated aliphatic hydrocarbon group having 1 to 10 carbon atoms, or a group $-(CO)-R^5$, wherein $R^5$ is a saturated aliphatic hydrocarbon group having 1 to 5 carbon atoms, d is an integer of 2 to 200, e is an integer of 0 to 200, provided that d+e is 2 to 200, and n is 2 to 6;

a is a value satisfying inequality $1.0 \leq a \leq 2.5$;

b is a value satisfying inequality $0.001 \leq b \leq 1.0$; and c is a value satisfying inequality $0.001 \leq c \leq 1.0$;

or an organohydrogenpolysiloxane represented by the following formula (2),

   (2)

wherein $R^1$ is the same as defined in formula (1), f is a value satisfying inequality $1.0 \leq f \leq 3.0$, and g is a value satisfying inequality $0.001 \leq g \leq 1.5$;

or a mixture of said organohydrogenpolysiloxanes of formulas (1) and (2); and (II) a polyoxyalkylene represented by the following formula (A)

   (A)

wherein h is an integer of 2 to 200, i is an integer of 0 to 200, provided that h+i is 2 to 200, and m is 2 to 6, or an organopolysiloxane represented by the following formula (B),

   (B)

wherein $R^1$ is the same as defined in formula (1), $R^4$ is a monovalent hydrocarbon group having an aliphatic unsaturated bond at the terminal thereof and containing 2 to 10 carbon atoms, j is a value satisfying inequality $1.0 \leq j \leq 3.0$, and k is a value satisfying inequality $0.001 \leq k \leq 1.5$, or a mixture of the polyoxyalkylene of formula (A) and the organopolysiloxane of formula (B), wherein at least one organohydrogenpolysiloxane of formula (1) or at least one polyoxyalkylene of formula (A) are contained as an essential component of the addition polymerization, (d) at least one water phase component, and (e) a cosmetic powder.

* * * * *

UNITED STATES PATENT AND TRADEMARK OFFICE
CERTIFICATE OF CORRECTION

PATENT NO. : 5,412,004

DATED : May 2, 1995

INVENTOR(S) : Tachibana et al.

It is certified that error appears in the above-indentified patent and that said Letters Patent is hereby corrected as shown below:

On the title page:

Item [30] Foreign Application Priority Data:

"3-189610" should read --4-189610--; and
"3-189611" should read --4-189611--.

Signed and Sealed this

Twenty-fifth Day of July, 1995

Attest:

BRUCE LEHMAN

*Attesting Officer*    *Commissioner of Patents and Trademarks*